United States Patent
Boral et al.

(10) Patent No.: US 9,567,324 B2
(45) Date of Patent: *Feb. 14, 2017

(54) SUBSTITUTED NICOTINAMIDE DERIVATIVES AS KINASE INHIBITORS

(71) Applicant: Allergan, Inc., Irvine, CA (US)

(72) Inventors: Sougato Boral, Santa Ana, CA (US); Shimiao Wang, Irvine, CA (US); Thomas C. Malone, Irvine, CA (US); Julie Wurster, Irvine, CA (US); Jie Shen, Irvine, CA (US); Michael Robinson, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/069,344

(22) Filed: Mar. 14, 2016

(65) Prior Publication Data

US 2016/0194311 A1 Jul. 7, 2016

Related U.S. Application Data

(63) Continuation of application No. 14/565,689, filed on Dec. 10, 2014, now abandoned.

(60) Provisional application No. 61/915,186, filed on Dec. 12, 2013, provisional application No. 61/915,209, filed on Dec. 12, 2013.

(51) Int. Cl.
| | | |
|---|---|---|
| *C07D 411/14* | (2006.01) | |
| *C07D 405/12* | (2006.01) | |
| *C07D 405/14* | (2006.01) | |
| *C07D 213/82* | (2006.01) | |
| *C07D 413/14* | (2006.01) | |
| *C07D 411/12* | (2006.01) | |

(52) U.S. Cl.
CPC .......... *C07D 413/14* (2013.01); *C07D 213/82* (2013.01); *C07D 405/12* (2013.01); *C07D 405/14* (2013.01); *C07D 411/12* (2013.01); *C07D 411/14* (2013.01)

(58) Field of Classification Search
IPC .............. C07D 411/14, 411/12, 413/14, 405/15, 213/82
See application file for complete search history.

(56) References Cited

FOREIGN PATENT DOCUMENTS

| WO | 2008061236 | 5/2008 |
| WO | 2013-062843 | 5/2013 |

OTHER PUBLICATIONS

Anderson et al, The Practice of Medicinal Chemistry, 1996, 32 Pages, 3rd Edition.
Arora, Amit et al, Role of Tyrosine Kinase Inhibitors in Cancer Therapy, Journal of Pharmacology and Experimental Therapeutics, 2005, 971-979, 315(3).
Barakat, Mark et al, VEGF Inhibitors for the Treatment of Neovascular Age-Related Macular Degeneration, Expert Opin. Investig. Drugs, 2009, 637-646, 18(5).
Berge, Stephen M., Pharmaceutical Salts, Journal of Pharmaceutical Sciences, Jan. 1977, 1-19, 66 (1), US.
Bergers, Gabriele et al, Benefits of Targeting Both Pericytes and Endothelial Cells in the Tumor Vasculature With Kinase Inhibitors, J. Clin. Invest., 2003, 1287-1295, 111.
Chappelow, Aimee et al, Neovascular Age-Related Macular Degeneration, Drugs, 2008, 1029-1036, 68 (8).
Cowan-Jacob, S.W., Structural Biology of Protein Tyrosine Kinases, Cell. Mol. Life Sci., 2006, 2608-2625, 63.
Dennis A. Smith, Do Prodrugs Deliver, Current Opinion in Drug Discovery & Development, 2007, 550-559, 10 (5), US.
Gould, Philip, Salt Selection for Basic Drugs, International Journal of Pharmaceutics, 1986, 201-217, 33.
Heinrich Stahl, Pharmaceutical Salts, Handbook of Pharmaceutical Salts, 2002, 329-345, International Union of Pure and Applied Chemistry, Verlag Helvetica Chemica Acta—Zürich.
Higuchi, T. et al, Pro-Drugs as Novel Drug Delivery Systems, 1975, 6 Pages.
Jo, Nobuo et al, Inhibition of Platelet-Derived Growth Factor B Signaling Enhances the Efficacy of Anti-Vascular Endothelial Growth Factor Therapy in Multiple Models of Ocular Neovascularization, American Journal of Pathology, Jun. 2006, 2036-2052, 168(6).
Ni, Zhang et al, Emerging Pharmacologic Therapies for Wet Age-Related Macular Degeneration, Ophthalmologica, 2009, 401-410, 223.
S. Roche, et al., Bilateral Congenital Idiopathic Talipes Equinovarus in Twins, Eur J. Orthop Surg Traumatol., 2004, 201-202, 14, US.
Stommel, J.M., et al., Coactivation of Receptor Tyrosine Kinases Affects the Response of Tumor Cells to TargetedTherapies, Science 2007, 318: 287-291.
Zhang, et al., Macroporous Alumina Monoliths Prepared by Filling Polymer Foams with Alumina Hydrogels, Journal of Materials Science, 2009, 931-938, 44, Springer Science.
PCT International Search Report and Written Opinion mailed on Mar. 10, 2015 for PCT/US2014/069601 filed on Dec. 10, 2014 in the name of Allergan, Inc.

*Primary Examiner* — Shirley V Gembeh
(74) *Attorney, Agent, or Firm* — Jonathan Bass

(57) ABSTRACT

The present invention relates to organic molecules capable of modulating tyrosine kinase signal transduction in order to regulate, modulate and/or inhibit abnormal cell proliferation.

17 Claims, No Drawings

SUBSTITUTED NICOTINAMIDE DERIVATIVES AS KINASE INHIBITORS

CROSS REFERENCE TO RELATED APPLICATIONS

This application is a continuation of U.S. patent application Ser. No. 14/565,689, filed Dec. 10, 2014, which in turn claims priority to and the benefit of U.S. Provisional Patent Application Nos. 61/915,186 and 61/915,209, each filed Dec. 12, 2013, the disclosures of which are hereby incorporated by reference in their entireties and serve as the basis of a priority and/or benefit claim for the present application.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life Sci., 2006, 63, 2608-2625 which is incorporated herein by reference.

There are a number of examples where RTK kinases, have been found to be involved in cellular signaling pathways leading to pathological conditions, including exudative age-related macular degeneration (Ni et al. Opthalmologica 2009 223 401-410; Chappelow et al. Drugs 2008 68 1029-1036), diabetic retinopathy (Zhang et al., Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105) and rosacea (Smith, J. R., V. B. Lanier, et al. *Br J Ophthalmol* 2007, 91(2): 226-229). In ophthalmic diseases such as exudative age-related macular degeneration and diabetic retinopathy aberrant activation of VEGF receptors can lead to abnormal blood vessel growth. The importance of VEGFR signaling in the exudative age-related macular degeneration disease process is evident by the clinical success of multiple anti-VEGF targeting agents including Lucentis®, Avastin®, and EYLEA™ (Barakat et al., Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as exudative age-related macular degeneration and diabetic retinopathy the inhibition of both VEGFR and PDGFRβ may provide a greater therapeutic effect by causing regression of existing neovascular blood vessels present in the disease (Adamis et al., Am. J. Pathol. 2006 168 2036-2053). In cancer inhibition of multiple RTK signaling pathways has been suggested to have a greater effect than inhibiting a single RTK pathway (De-Pinho et al., Science 2007 318 287-290; Bergers et al. J. Clin Invest. 2003 111 1287-1295).

WO 2013/062843 A1 refers to pyridine-sulfoximines as tyrosine kinase inhibitors.

WO 2008/061236 A2 refers to sulfoximine-nicotine derivatives as kinase inhibitors and their preparation, pharmaceutical compositions and use in the treatment of proliferative diseases.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

The above references are hereby incorporated by reference in their entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction by blocking the VEGF and/or PDGF receptors. Such compounds are useful for the treatment of diseases related to unregulated tyrosine kinase signal transduction, including vascular proliferative disorders such as diabetic retinopathy, age-related macular degeneration and retinopathy of prematurity.

In one illustrative embodiment, the compounds of the present invention have the following general formula I:

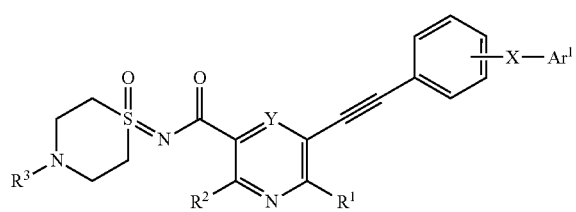

wherein
$R^1$ is hydrogen or $NH_2$
$R^2$ is hydrogen or $NH_2$

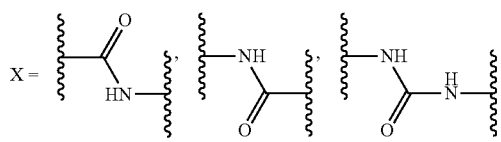

Y is CH or N
$Ar^1$ is an aryl, i.e. a carbocyclic aryl or a heteroaryl group,
$R^3$ is hydrogen or lower alkyl, or

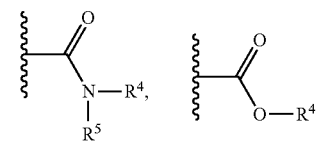

$R^4$ is hydrogen, lower alkyl, $(CH_2)_nCOOR^6$ or $(CH_2)_nCOR^7$,
$R^5$ is hydrogen or lower alkyl,
$R^6$ is hydrogen or lower alkyl,
$R^7$ is an amine, e.g. a substituted amine, which may be selected from the group consisting of

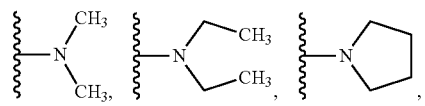

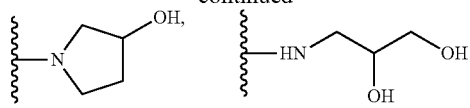

and n is 0, or an integer of from 1 to 6 and further including prodrugs, pharmaceutically acceptable salts, racemic mixtures and enantiomers thereof.

Preferably, in formula I, X is —NH—C(O)—.
Preferably, in formula I, Y is CH.
Preferably, in formula I, $Ar^1$ is elected from the group consisting of phenyl and furanyl, e.g. lower alkyl and/or halo-substituted phenyl and furanyl. Most preferably $Ar^1$ is selected from the group consisting of 3-methyl-2-furanyl and 2-fluoro-5-methylphenyl.
Preferably, in formula I, $R^2$ is H.
Preferably, in formula I, $R^3$ is selected from the group consisting of

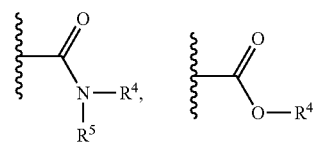

wherein $R^4$ and $R^5$ are as defined above.
More preferably in formula I, $R^3$ is selected from the group consisting of —C(O)N($R^4$)($R^5$)
wherein $R^4$ and $R^5$ are as defined above.

In another illustrative embodiment, the compounds of the present invention have the following general formula II:

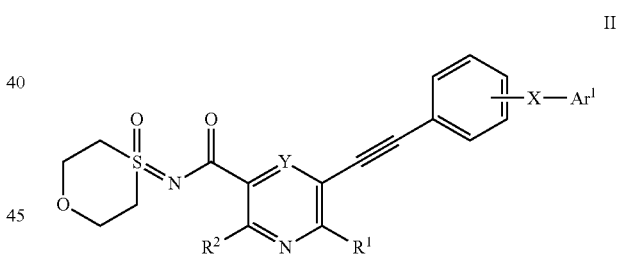

wherein
$R^1$ is hydrogen or $NH_2$
$R^2$ is hydrogen or $NH_2$
X is

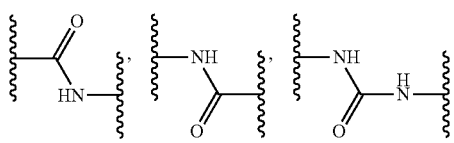

Y is CH or N
$Ar^1$ is an aryl group, i.e. a carbocyclic aryl group or heteroaryl group, further including prodrugs, pharmaceutically acceptable salts, racemic mixtures and enantiomers thereof. Said carbocyclic aryl or heteroaryl group may be optionally substituted with one or more alkoxy, halogen, trihaloalkyl (e.g., trifluoromethyl), or lower alkyl radicals.

Preferably, in formula II, X is —NHC(O)— or —C(O)NH—

Preferably, in formula II, Y is CH.

Preferably, in formula II, $Ar^1$ is selected from the group consisting of phenyl, oxazoyl and furanyl and lower alkyl, alkyloxy and/or halo-substituted phenyl, oxazoyl and furanyl.

Most preferably in formula II, $Ar^1$ is selected from the group consisting of
3-methylfuranyl, 2-fluoro 5-methylphenyl, 4-chloro 5-t-butylphenyl, 3-methoxyphenyl and
5-butyloxazoyl.

Preferably, in formula II, $R^2$ is H.

Most preferably, said compounds of formulae I and II are selected from the group consisting of:

tert-butyl 1-({[5-({3-[(3-methyl-2-furoyl)amino]phenyl}ethynyl)pyridin-3-yl]carbonyl}imino)-1$\lambda^4$,4-thiazinane-4-carboxylate 1-oxide 1-({[5-({3-[(3-methyl-2-furoyl)amino]phenyl}ethynyl)pyridin-3-yl]carbonyl}imino)-1$\lambda^4$,4-thiazinane-4-carboxamide 1-oxide 1-({[5-({3-[(3-methyl-2-furoyl)amino]phenyl}ethynyl)pyridin-3-yl]carbonyl}imino)-1$\lambda^4$,4-thiazinane-4-carboxamide 1-oxide ethyl 3-({[1-({[5-({3-[(3-methyl-2-furoyl)amino]phenyl}ethynyl)pyridin-3-yl]carbonyl}imino)-1-oxido-1$\lambda^4$,4-thiazinan-4-yl]carbonyl}amino)propanoate ethyl 4-({[1-({[5-({3-[(3-methyl-2-furoyl)amino]phenyl}ethynyl)pyridin-3-yl]carbonyl}imino)-1-oxido-1$\lambda^4$,4-thiazinan-4-yl]carbonyl}amino)butanoate 3-({[1-({[5-({3-[(3-methyl-2-furoyl)amino]phenyl}ethynyl)pyridin-3-yl]carbonyl}imino)-1-oxido-1$\lambda^4$,4-thiazinan-4-yl]carbonyl}amino)propanoic acid 4-({[1-({[5-({3-[(3-methyl-2-furoyl)amino]phenyl}ethynyl)pyridin-3-yl]carbonyl}imino)-1-oxido-1$\lambda^4$,4-thiazinan-4-yl]carbonyl}amino)butanoic acid N-[3-(3-hydroxypyrrolidin-1-yl)-3-oxopropyl]-1-({[5-({3-[(3-methyl-2-furoyl)amino]phenyl}ethynyl)pyridin-3-yl]carbonyl}imino)-1$\lambda^4$,4-thiazinane-4-carboxamide 1-oxide N-[4-(3-hydroxypyrrolidin-1-yl)-4-oxobutyl]-1-({[5-({3-[(3-methyl-2-furoyl)amino]phenyl}ethynyl)pyridin-3-yl]carbonyl}imino)-1$\lambda^4$,4-thiazinane-4-carboxamide 1-oxide N-{4-[(2,3-dihydroxypropyl)amino]-4-oxobutyl}-1-({[5-({3-[(3-methyl-2-furoyl)amino]phenyl}ethynyl)pyridin-3-yl]carbonyl}imino)-1$\lambda^4$,4-thiazinane-4-carboxamide 1-oxide ethyl ({[1-({[5-({3-[(3-methyl-2-furoyl)amino]phenyl}ethynyl)pyridin-3-yl]carbonyl}imino)-1-oxido-1$\lambda^4$,4-thiazinan-4-yl]carbonyl}amino)acetate ({[1-({[5-({3-[(3-methyl-2-furoyl)amino]phenyl}ethynyl)pyridin-3-yl]carbonyl}imino)-1-oxido-1$\lambda^4$,4-thiazinan-4-yl]carbonyl}amino)acetic acid tert-butyl 1-({[6-amino-5-({3-[(3-methyl-2-furoyl)amino]phenyl}ethynyl)pyridin-3-yl]carbonyl}imino)-1$\lambda^4$,4-thiazinane-4-carboxylate 1-oxide 6-amino-5-({3-[(3-methyl-2-furoyl)amino]phenyl}ethynyl)-N-(1-oxido-1$\lambda^4$,4-thiazinan-1-ylidene)nicotinamide 1-({[6-amino-5-({3-[(3-methyl-2-furoyl)amino]phenyl}ethynyl)pyridin-3-yl]carbonyl}imino)-1$\lambda^4$,4-thiazinane-4-carboxamide 1-oxide tert-butyl 1-({[6-amino-5-({3-[(2-fluoro-5-methylbenzoyl)amino]phenyl}ethynyl)pyridin-3-yl]carbonyl}imino)-1$\lambda^4$,4-thiazinane-4-carboxylate 1-oxide 6-amino-5-({3-[(2-fluoro-5-methylbenzoyl)amino]phenyl}ethynyl)-N-(1-oxido-1$\lambda^4$,4-thiazinan-1-ylidene)nicotinamide 1-({[6-amino-5-({3-[(2-fluoro-5-methylbenzoyl)amino]phenyl}ethynyl)pyridin-3-yl]carbonyl}imino)-1$\lambda^4$,4-thiazinane-4-carboxamide 1-oxide 5-({3-[(3-methyl-2-furoyl)amino]phenyl}ethynyl)-N-(4-oxido-1,4$\lambda^4$-oxathian-4-ylidene)nicotinamide, 6-amino-5-({3-[(3-methyl-2-furoyl)amino]phenyl}ethynyl)-N-(4-oxido-1,4$\lambda^4$-oxathian-4-ylidene)nicotinamide, 6-amino-5-({3-[(2-fluoro-5-methylbenzoyl)amino]phenyl}ethynyl)-N-(4-oxido-1,4$\lambda^4$-oxathian-4-ylidene)nicotinamide, 6-amino-5-[(3-{[(2-fluoro-5-methylphenyl)amino]carbonyl}phenyl)ethynyl]-N-(4-oxido-1,4$\lambda^4$-oxathian-4-ylidene)nicotinamide, 6-amino-5-{[3-({[4-chloro-3-(trifluoromethyl)phenyl]amino}carbonyl)phenyl]ethynyl}-N-(4-oxido-1,4$\lambda^4$-oxathian-4-ylidene)nicotinamide, 6-amino-5-[(3-{[(5-tert-butylisoxazol-3-yl)amino]carbonyl}phenyl)ethynyl]-N-(4-oxido-1,4$\lambda^4$-oxathian-4-ylidene)nicotinamide and 6-amino-5-[(3-{[(3-methoxyphenyl)amino]carbonyl}phenyl)ethynyl]-N-(4-oxido-1,4$\lambda^4$-oxathian-4-ylidene)nicotinamide.

Compounds of formulae I and II are useful as kinase inhibitors. As such, compounds of formula I will be useful for treating diseases related to unregulated tyrosine kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, pterigium, arthritis, restenosis, hepatic cirrhosis, atherosclerosis, psoriasis, rosacea, diabetis mellitus, wound healing, and neurodegenerative diseases and preferably ophthalmic diseases, i.e. diabetic retinopathy, age-related macular degeneration, retinopathy of prematurity, pterygia, blepharoconjunctivitis, chronic allergic conjunctivitis, recurrent episcleritis, keratoconjunctivitis sicca. In addition the following dermatological indications may be treated with the compounds of this invention: sun burn, eczema, psoriasis, contact dermatitis.

DETAILED DESCRIPTION OF THE INVENTION

The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy. The compositions of the present invention are also useful in treating pterygia, blepharoconjunctivitis, chronic allergic conjunctivitis, recurrent episcleritis, keratoconjunctivitis sicca. In addition the following dermatological indications may be treated: sun burn, eczema, psoriasis contact dermatitis.

Most preferably, the compounds of the present invention are useful an ophthalmic disease, wherein said ophthalmic disease is selected from the group consisting of pterygia, hyperemia related to an actively inflamed pterygia, recurrent pterygia following excisional surgery, prophylactic therapy to prevent recurrent pterygia post-excision, progressive pterygia approaching the visual axis, chronic low grade hyperemia associated with pterygia, corneal neovascularization, neovascular glaucoma, iris neovascularization, chronic allergic conjunctivitis, ocular rosacea, blepharoconjunctivitis, recurrent episcleritis, keratoconjunctivitis sicca, ocular graft vs host disease, diabetic retinopathy, diabetic macular edema, proliferative diabetic retinopathy, exudative or neovascular age-related macular degeneration, high-risk eyes (i.e. fellow eyes have neovascular age-related macular degeneratuon) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, idiopathic etiologies, presumed ocular histoplasmosis syndrome, and retinopathy of prematurity.

The following defined terms are used throughout this specification:
"BOP" refers to benzotriazol-1-yloxytris(dimethylamino)phosphoniumhexafluorophosphate
"BOC" refers to ditertiarybutyldicarbonate
"DCM" refers to dichloromethane
"DIPEA" refers to diisopropylethylamine
"DMAP" refers to dimethylformamide
"DMF" refers to dimethylformamide
"EDCI" refers to N-(3-Dimethylaminopropyl)-N'-ethylcarbodiimide
"PDGF" refers to platelet derived growth factor.
"PDGFR" refers to platelet derived growth factor receptor.
"Ph" refers to phenyl
"PTK" refers to protein tyrosine kinase
"RT" refers to room temperature
"RTK" refers to receptor tyrosine kinase
"THF" refers to tetrahydrofuran
"VEGF" refers to vascular endothelial growth factor
"VEGFR" refers to vascular endothelial growth factor receptor "Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halo, nitrogen, oxygen, sulfur or phosphorus atom, e.g. fluoro, chloro, cyano, nitro, dialkylamino, hydroxyl, phosphate, thiol, etc.

The compounds of Formulae I and II can form salts which are also within the scope of this invention. Reference to a compound of Formula I or II herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I or II contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formulae I and II may be formed, for example, by reacting a compound of Formula I or II with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others. All such acid salts and base salts are intended to be pharmaceutically acceptable salts within the scope of the invention and all acid and base salts are considered equivalent to the free forms of the corresponding compounds for purposes of the invention.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. 25 Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkoxy" refers to O-alkyl.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl (e.g., trifluoromethyl), hydroxyl, SH, OH, $NO_2$, amine, thioether, cyano, alkoxy, alkyl, and amino.

"Carbocyclic aryl" refers to an aryl group wherein the ring atoms are carbon "Heteroaryl" or "heterocyclic aryl" refers to an aryl group having from 1 to 3 heteroatoms as ring atoms, the remainder of the ring atoms being carbon. Heteroatoms include oxygen, sulfur, and nitrogen. Thus, heteroaryl groups include furanyl, thienyl, pyridyl, pyrrolyl, N-lower alkyl pyrrolo, pyrimidyl, pyrazinyl, imidazolyl and the like.

"Heterocyclic" refers to cyclic group having at least one enchained heteroatom and includes aromatic and non-aromatic cyclic groups.

Specific examples of the compounds of the invention and the structures of said compounds are given in the table, below. However, the invention is not limited to the following compounds and structures.

| Example | Structure | Compound Name |
|---|---|---|
| 1 | 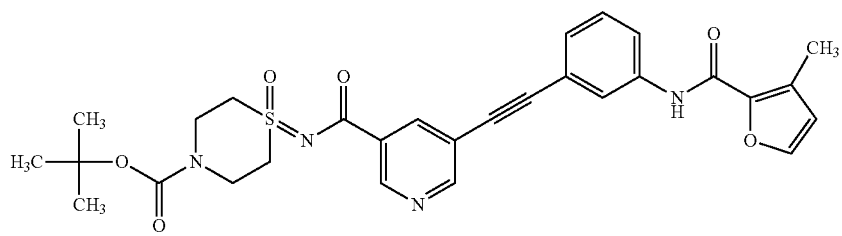 [SMILES: Cc1ccoc1C(=O)Nc1cccc(C#Cc2cncc(C(=O)N=S3(=O)CCN(C(=O)OC(C)(C)C)CC3)c2)c1] | tert-butyl 1-({[5-({3-[(3-methyl-2-furoyl)amino] phenyl}ethynyl) pyridin-3-yl] carbonyl}imino)-1 $\lambda^4$,4-thiazinane-4-carboxylate 1-oxide |
| 2 | 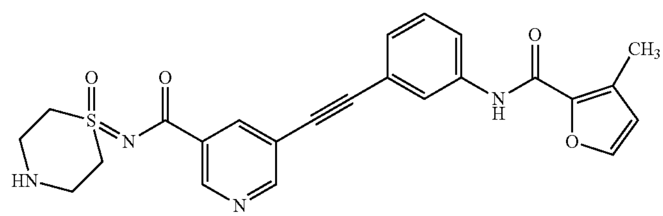 [SMILES: Cc1ccoc1C(=O)Nc1cccc(C#Cc2cncc(C(=O)N=S3(=O)CCNCC3)c2)c1] | 5-({3-[(3-Methyl-2-furoyl)amino] phenyl}ethynyl)-N-(1-oxido-1 $\lambda^4$,4-thiazinan-1-ylidene) nicotinamide |
| 3 | 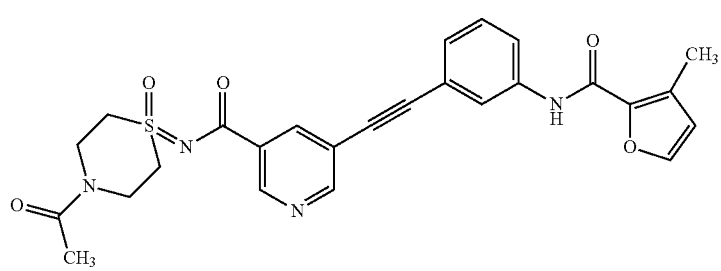 | 1-({[5-({3-[(3-methyl-2-furoyl) amino]phenyl} ethynyl)pyridin-3-yl]carbonyl} imino)-1 $\lambda^4$,4-thiazinane-4-carboxamide 1-oxide |
| 4 | 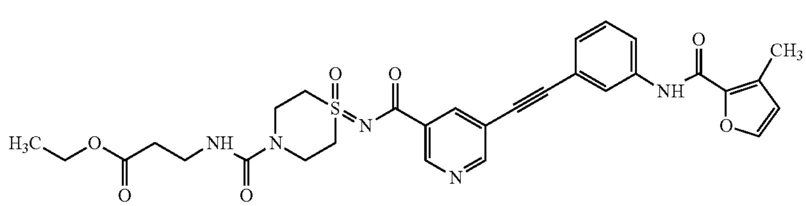 [SMILES: CCOC(=O)CCNC(=O)N1CCS(=O)(=NC(=O)c2cncc(C#Cc3cccc(NC(=O)c4occc4C)c3)c2)CC1] | ethyl 3-({[1-({[5-({3-[(3-methyl-2-furoyl)amino] phenyl}ethynyl) pyridin-3-yl] carbonyl}imino)-1-oxido-1 $\lambda^4$,4-thiazinan-4-yl]carbonyl} amino)propanoate |

-continued

| Example | Structure | Compound Name |
|---|---|---|
| 5 | 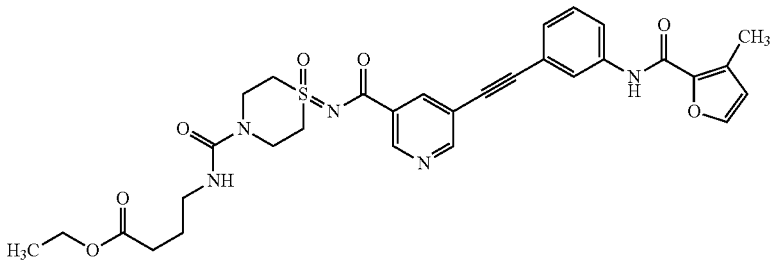 [SMILES: CCOC(=O)CCCNC(=O)N1CCS(=O)(=NC(=O)c2cncc(C#Cc3cccc(NC(=O)c4occc4C)c3)c2)CC1] | ethyl 4-({[1-({[5-({3-[(3-methyl-2-furoyl)amino]phenyl}ethynyl)pyridin-3-yl]carbonyl}imino)-1-oxido-1 $\lambda^4$,4-thiazinan-4-yl]carbonyl}amino)butanoate |
| 6 | 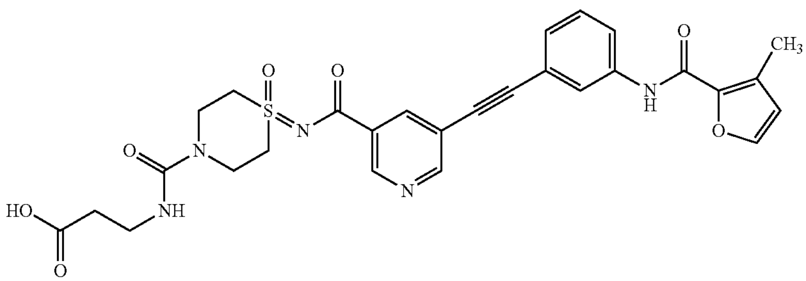 [SMILES: Cc1ccoc1C(=O)Nc1cccc(C#Cc2cncc(C(=O)N=S3(=O)CCN(C(=O)NCCC(=O)O)CC3)c2)c1] | 3-({[1-({[5-({3-[(3-methyl-2-furoyl)amino]phenyl}ethynyl)pyridin-3-yl]carbonyl}imino)-1-oxido-1 $\lambda^4$,4-thiazinan-4-yl]carbonyl}amino)propanoic acid |
| 7 | 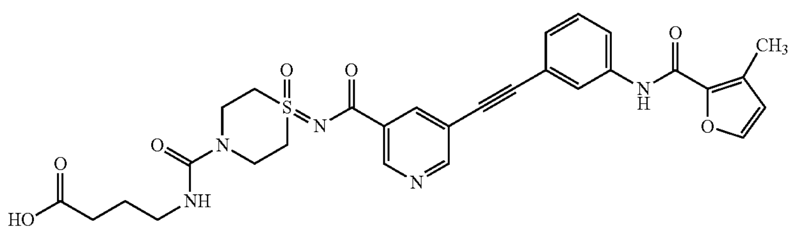 [SMILES: Cc1ccoc1C(=O)Nc1cccc(C#Cc2cncc(C(=O)N=S3(=O)CCN(C(=O)NCCCC(=O)O)CC3)c2)c1] | 4-({[1-({[5-({3-[(3-methyl-2-furoyl)amino]phenyl}ethynyl)pyridin-3-yl]carbonyl}imino)-1-oxido-1 $\lambda^4$,4-thiazinan-4-yl]carbonyl}amino)butanoic acid |
| 8 | 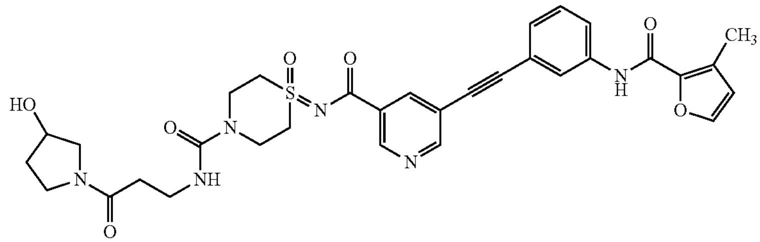 [SMILES: Cc1ccoc1C(=O)Nc1cccc(C#Cc2cncc(C(=O)N=S3(=O)CCN(C(=O)NCCC(=O)N4CCC(O)C4)CC3)c2)c1] | N-[3-(3-hydroxy-pyrrolidin-1-yl)-3-oxopropyl]-1-({[5-({3-[(3-methyl-2-furoyl)amino]phenyl}ethynyl)pyridin-3-yl]carbonyl}imino)-1 $\lambda^4$,4-thiazinane-4-carboxamide 1-oxide |
| 9 | 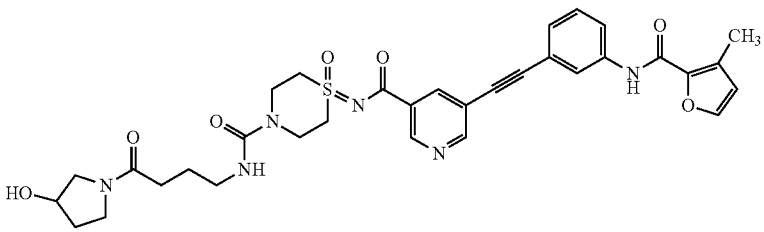 [SMILES: Cc1ccoc1C(=O)Nc1cccc(C#Cc2cncc(C(=O)N=S3(=O)CCN(C(=O)NCCCC(=O)N4CCC(O)C4)CC3)c2)c1] | N-[4-(3-hydroxy-pyrrolidin-1-yl)-4-oxobutyl]-1-({[5-({3-[(3-methyl-2-furoyl)amino]phenyl}ethynyl)pyridin-3-yl]carbonyl}imino)-1 $\lambda^4$,4-thiazinane-4-carboxamide 1-oxide |

-continued

| Example | Structure | Compound Name |
|---|---|---|
| 10 | 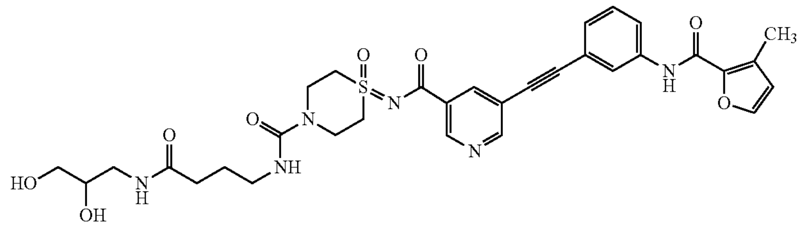 [SMILES: Cc1ccoc1C(=O)Nc1cccc(C#Cc2cncc(C(=O)N=S3(=O)CCN(C(=O)NCCCC(=O)NCC(O)CO)CC3)c2)c1] | N-{4-[(2,3-dihydroxypropyl)amino]-4-oxobutyl}-1-({[5-({3-[(3-methyl-2-furoyl)amino]phenyl}ethynyl)pyridin-3-yl]carbonyl}imino)-1 $\lambda^4$,4-thiazinane-4-carboxamide 1-oxide |
| 11 | 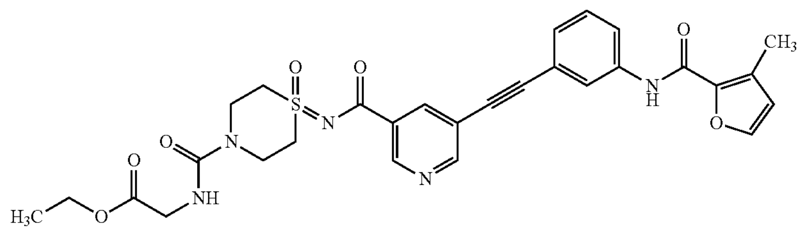 [SMILES: CCOC(=O)CNC(=O)N1CCS(=O)(=NC(=O)c2cncc(C#Cc3cccc(NC(=O)c4occc4C)c3)c2)CC1] | ethyl ({[1-({[5-({3-[(3-methyl-2-furoyl)amino]phenyl}ethynyl)pyridin-3-yl]carbonyl}imino)-1-oxido-1 $\lambda^4$,4-thiazinan-4-yl]carbonyl}amino)acetate |
| 12 | 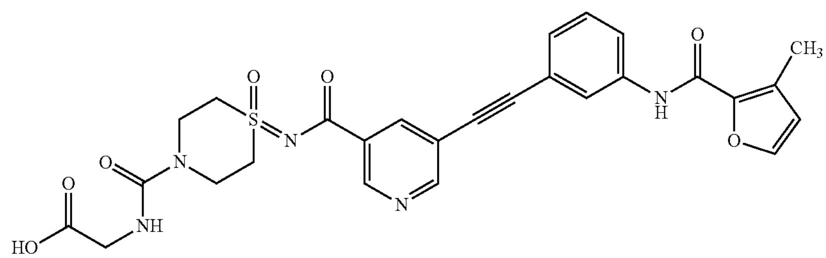 [SMILES: Cc1ccoc1C(=O)Nc1cccc(C#Cc2cncc(C(=O)N=S3(=O)CCN(C(=O)NCC(=O)O)CC3)c2)c1] | ({[1-({[5-({3-[(3-methyl-2-furoyl)amino]phenyl}ethynyl)pyridin-3-yl]carbonyl}imino)-1-oxido-1 $\lambda^4$,4-thiazinan-4-yl]carbonyl}amino)acetic acid |
| 13 | 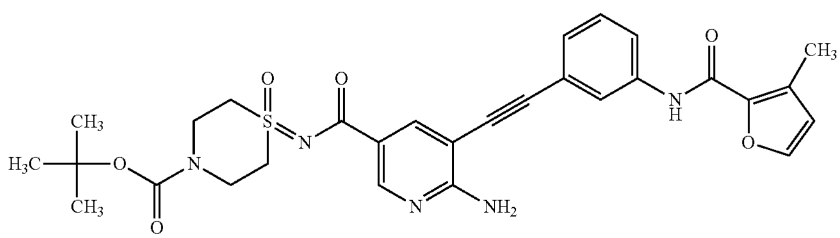 [SMILES: Cc1ccoc1C(=O)Nc1cccc(C#Cc2cc(C(=O)N=S3(=O)CCN(C(=O)OC(C)(C)C)CC3)cnc2N)c1] | tert-butyl 1-({[6-amino-5-({3-[(3-methyl-2-furoyl)amino]phenyl}ethynyl)pyridin-3-yl]carbonyl}imino)-1 $\lambda^4$,4-thiazinane-4-carboxylate 1-oxide |
| 14 | 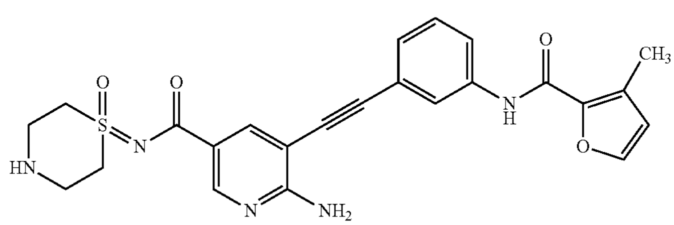 [SMILES: Cc1ccoc1C(=O)Nc1cccc(C#Cc2cc(C(=O)N=S3(=O)CCNCC3)cnc2N)c1] | 6-amino-5-({3-[(3-methyl-2-furoyl)amino]phenyl}ethynyl)-N-(1-oxido-1 $\lambda^4$,4-thiazinan-1-ylidene)nicotinamide |
| 15 | 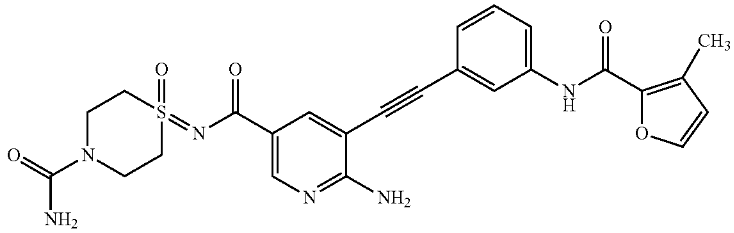 [SMILES: Cc1ccoc1C(=O)Nc1cccc(C#Cc2cc(C(=O)N=S3(=O)CCN(C(N)=O)CC3)cnc2N)c1] | 1-({[6-amino-5-({3-[(3-methyl-2-furoyl)amino]phenyl}ethynyl)pyridin-3-yl]carbonyl}imino)-1 $\lambda^4$,4-thiazinane-4-carboxamide 1-oxide |

-continued

| Example | Structure | Compound Name |
|---|---|---|
| 16 | 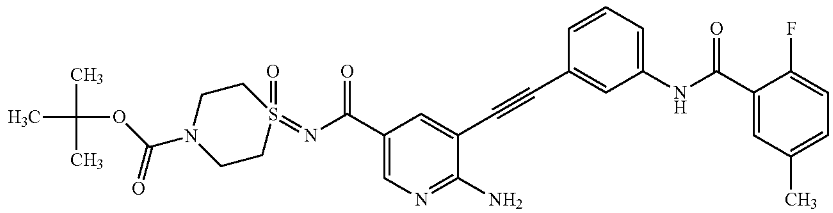 | tert-butyl 1-({[6-amino-5-({3-[(2-fluoro-5-methylbenzoyl)amino]phenyl}ethynyl)pyridin-3-yl]carbonyl}imino)-1 $\lambda^4$,4-thiazinane-4-carboxylate 1-oxide |
| 17 | 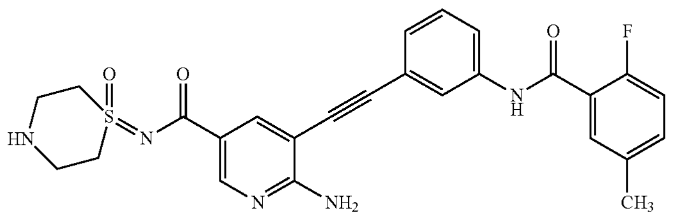 [SMILES: Cc1ccc(F)c(C(=O)Nc2cccc(C#Cc3cc(C(=O)N=S4(=O)CCNCC4)cnc3N)c2)c1] | 6-amino-5-({3-[(2-fluoro-5-methylbenzoyl)amino]phenyl}ethynyl)-N-(1-oxido-1 $\lambda^4$,4-thiazinan-1-ylidene)nicotinamide |
| 18 | 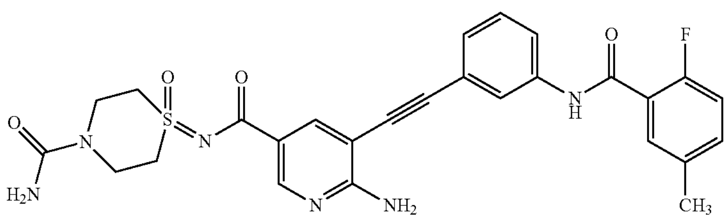 [SMILES: Cc1ccc(F)c(C(=O)Nc2cccc(C#Cc3cc(C(=O)N=S4(=O)CCN(C(N)=O)CC4)cnc3N)c2)c1] | 1-({[6-amino-5-({3-[(2-fluoro-5-methylbenzoyl)amino]phenyl}ethynyl)pyridin-3-yl]carbonyl}imino)-1 $\lambda^4$,4-thiazinane-4-carboxamide 1-oxide |
| 19 | 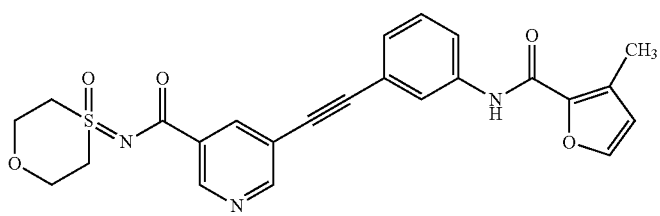 [SMILES: Cc1ccoc1C(=O)Nc1cccc(C#Cc2cncc(C(=O)N=S3(=O)CCOCC3)c2)c1] | 5-({3-[(3-methyl-2-furoyl)amino]phenyl}ethynyl)-N-(4-oxido-1,4$\lambda^4$-oxathian-4-ylidene)nicotinamide |
| 20 | 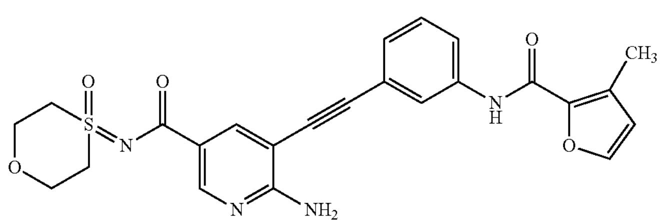 [SMILES: Cc1ccoc1C(=O)Nc1cccc(C#Cc2cc(C(=O)N=S3(=O)CCOCC3)cnc2N)c1] | 6-amino-5-({3-[(3-methyl-2-furoyl)amino]phenyl}ethynyl)-N-(4-oxido-1,4$\lambda^4$-oxathian-4-ylidene)nicotinamide |
| 21 | 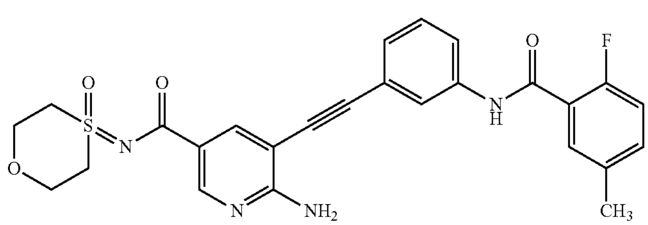 [SMILES: Cc1ccc(F)c(C(=O)Nc2cccc(C#Cc3cc(C(=O)N=S4(=O)CCOCC4)cnc3N)c2)c1] | 6-amino-5-({3-[(2-fluoro-5-methylbenzoyl)amino]phenyl}ethynyl)-N-(4-oxido-1,4$\lambda^4$-oxathian-4-ylidene)nicotinamide |

| Example | Structure | Compound Name |
|---|---|---|
| 22 | 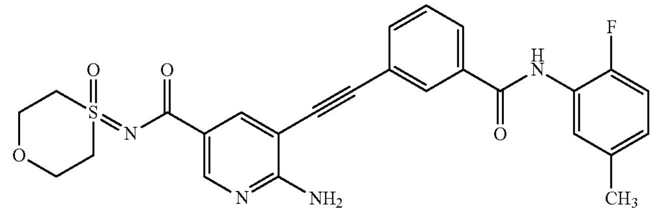 [SMILES: Cc1ccc(F)c(NC(=O)c2cccc(C#Cc3cc(C(=O)N=S4(=O)CCOCC4)cnc3N)c2)c1] | 6-amino-5-[(3-{[(2-fluoro-5-methylphenyl)amino]carbonyl}phenyl)ethynyl]-N-(4-oxido-1,4λ⁴-oxathian-4-ylidene)nicotinamide |
| 23 | 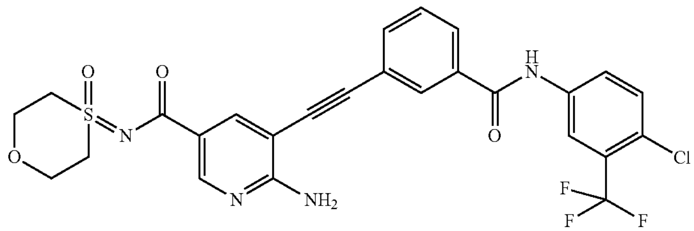 [SMILES: Nc1ncc(C(=O)N=S2(=O)CCOCC2)cc1C#Cc1cccc(C(=O)Nc2ccc(Cl)c(C(F)(F)F)c2)c1] | 6-amino-5-{[3-({[4-chloro-3-(trifluoromethyl)phenyl]amino}carbonyl)phenyl]ethynyl}-N-(4-oxido-1,4λ⁴-oxathian-4-ylidene)nicotinamide |
| 24 | 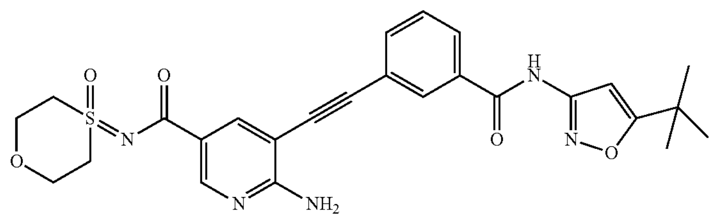 [SMILES: CC(C)(C)c1cc(NC(=O)c2cccc(C#Cc3cc(C(=O)N=S4(=O)CCOCC4)cnc3N)c2)no1] | 6-amino-5-[(3-{[(5-tert-butylisoxazol-3-yl)amino]carbonyl}phenyl)ethynyl]-N-(4-oxido-1,4λ⁴-oxathian-4-ylidene)nicotinamide |
| 25 | 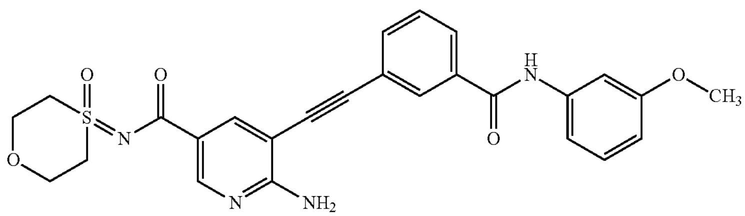 [SMILES: COc1cccc(NC(=O)c2cccc(C#Cc3cc(C(=O)N=S4(=O)CCOCC4)cnc3N)c2)c1] | 6-amino-5-[(3-{[(3-methoxyphenyl)amino]carbonyl}phenyl)ethynyl]-N-(4-oxido-1,4λ⁴-oxathian-4-ylidene)nicotinamide |

Routes to compounds of formula I are illustrated by but not limited to the schemes provided below:

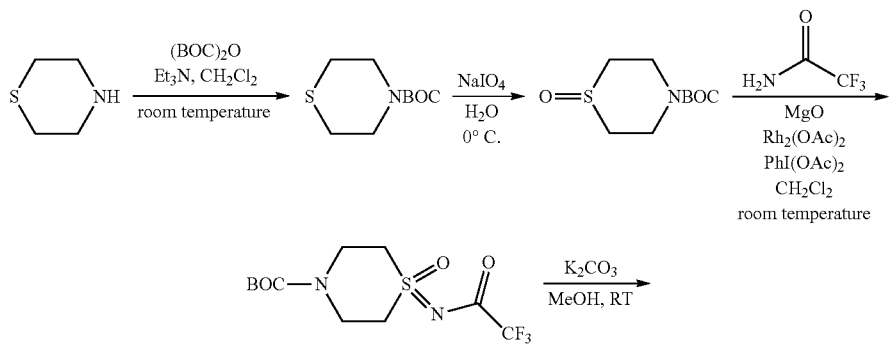

Scheme 1

-continued
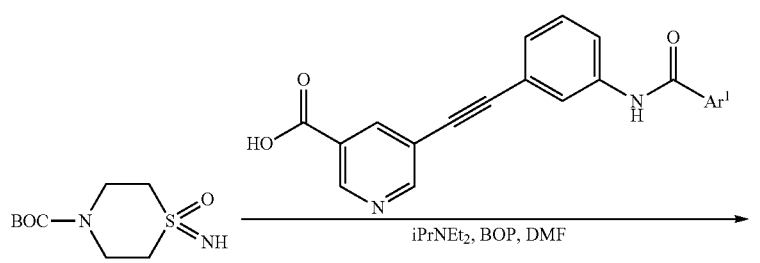
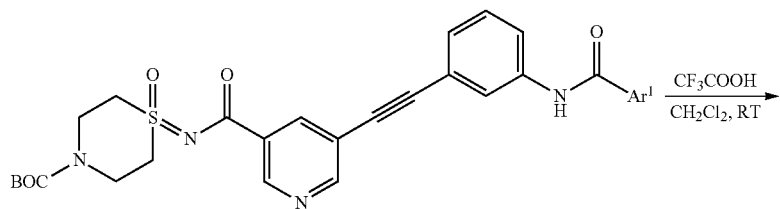
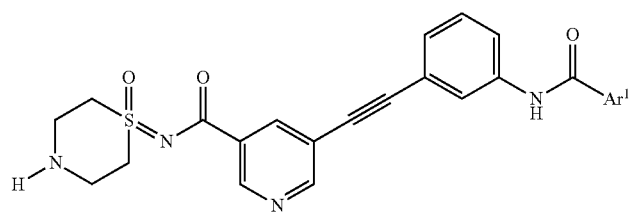
Scheme 2
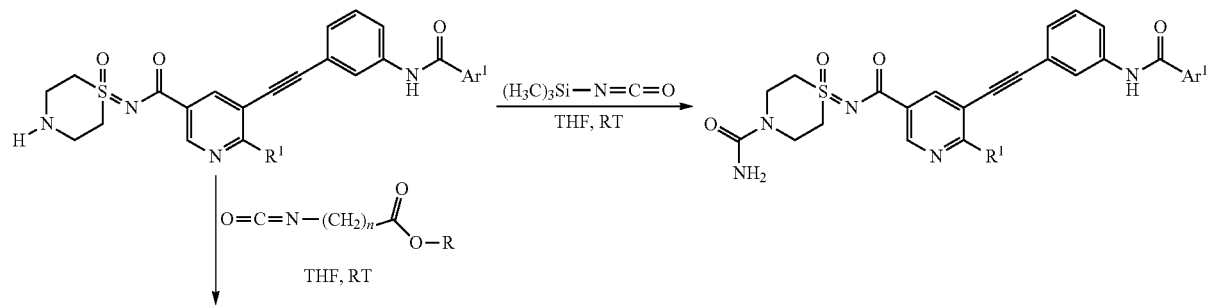
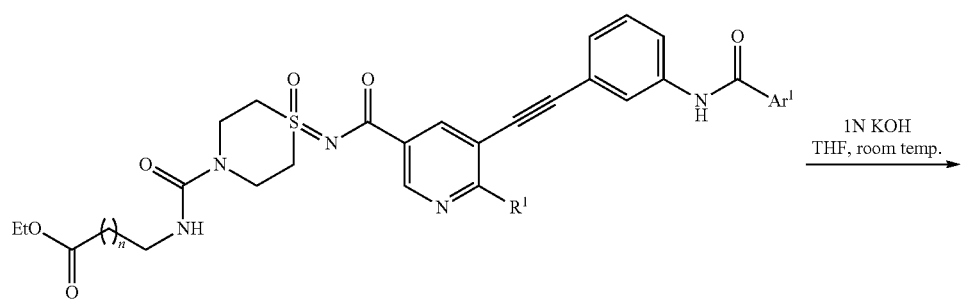

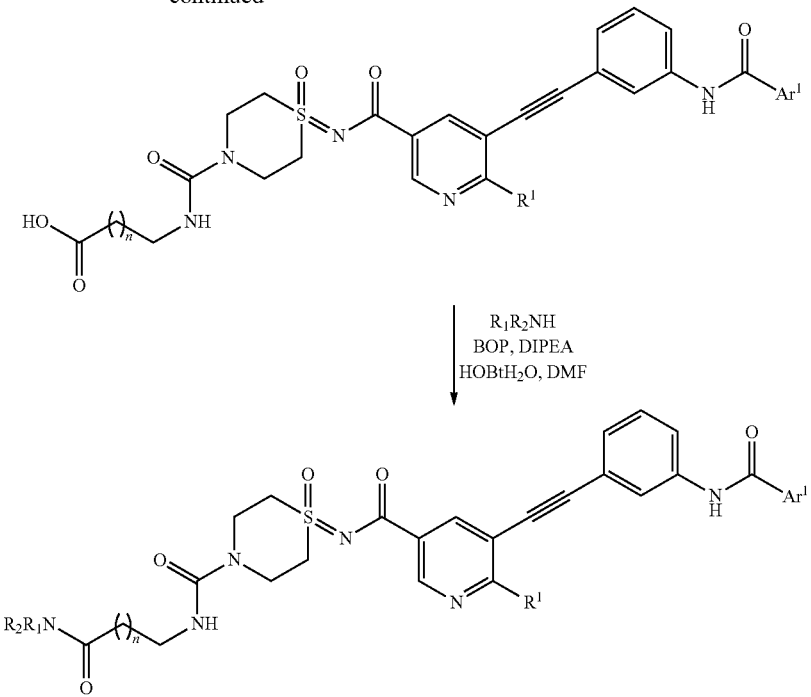
n = 0, 1, 2
Routes to compounds of formula II are illustrated by but not limited to the schemes provided below:
Scheme 3
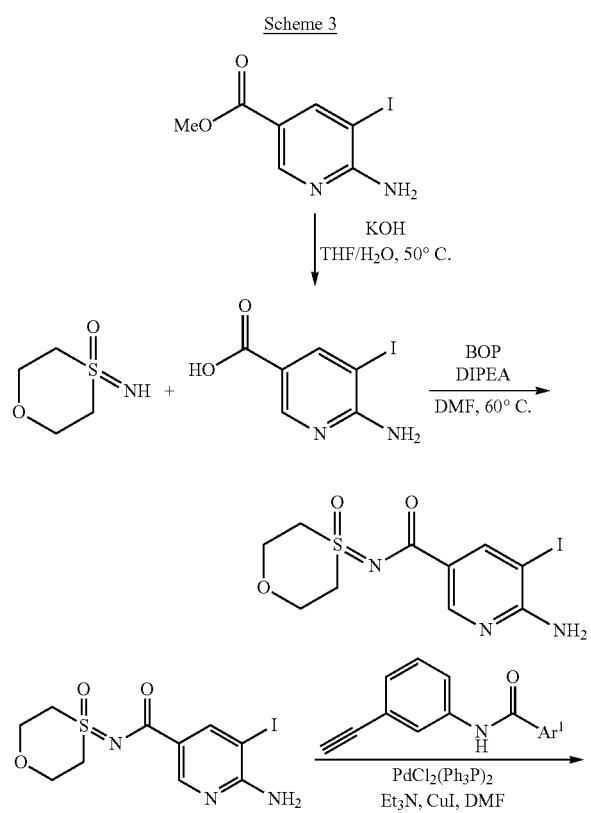
Scheme 4
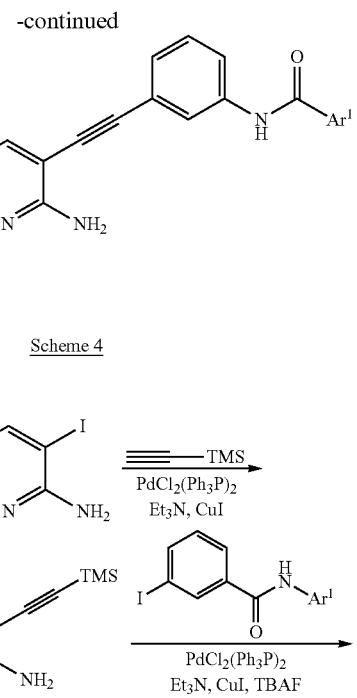

The invention is further illustrated by the following nonlimiting Examples.

Preparation 1

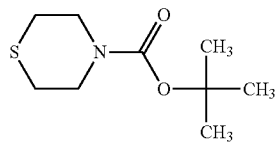

tert-Butyl thiomorpholine-4-carboxylate

To a solution of thiomorpholine (4.84 mL, 50 mmol, 1 eq) in DCM (200 mL) was added Et$_3$N (14.6 mL, 2.1 eq) and di-tert-butyldicarbonate (12.0 g, 1.1 eq) with stirring under nitrogen atmosphere. The resulting clear solution was stirred at RT for an overnight. The reaction solution was washed with H$_2$O (1×), aqueous NH$_4$Cl (1×), brine (1×) and dried over anhydrous MgSO$_4$. The organic solution was filtered through a pad of celite and the filtrate concentrated. The white solid residue was treated with EtOAc-hexane (1:25) with stirring and then cooled in fridge for 30 min. The white solid which formed was collected to give the title compound as a white crystalline solid (10.1 g, quantitative). $^1$H NMR (DMSO-d$_6$) δ: 3.54-3.59 (m, 4H), 2.48-2.54 (m, 4H), 1.40 (s, 9H)

Preparation 2

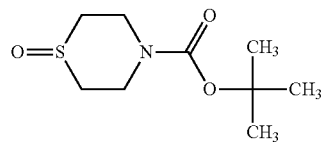

tert-Butyl thiomorpholine-4-carboxylate 1-oxide

In a 250 mL round-bottom flask equipped with a magnetic stirrer were placed powdered sodium metaperiodate (5.68 g, 1.05 eq) and water (50 mL). The mixture was stirred at RT first and then cooled to 0° C., followed by the addition of tert-butyl thiomorpholine-4-carboxylate (5.08 g, 25 mmol, 1 eq). Then to this mixture was added dixane (30 mL) and MeOH (40 mL). The reaction mixture was stirred at 0° C. for 5.5 hours. It was then filtered through a Buchner funnel, the white solid was washed with CHCl$_3$ (3×50 mL), and the resulting water-chloroform filtrate was transferred into a separation funnel. The lower chloroform was removed and the aqueous layer was extracted with CHCl$_3$ (3×150 mL). The organic phases were combined and dried over anhydrous Na$_2$SO$_4$ overnight. The upper clear layer was then decanted and concentrated to give the title compound as white solid (5.41 g, 99%). $^1$H NMR (DMSO-d$_6$) δ: 3.81 (d, J=13.4 Hz, 2H), 3.60 (br. s., 2H), 2.76-2.84 (m, 2H), 2.65-2.71 (m, 2H), 1.41 (s, 9H)

Preparation 3

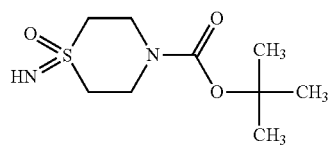

tert-Butyl 1-imino-1λ$^4$,4-thiazinane-4-carboxylate 1-oxide

Trifluoroacetamide (5.82 g, 2 eq), magnesium oxide (4.05 g, 4 eq), and rhodium(II) acetate dimer (330 mg, 0.03 eq) were placed in a 250 mL round bottom flask. Dichloromethane (70 mL) under a nitrogen atmosphere was then added with stirring, followed by the addition of tert-butyl thiomorpholine-4-carboxylate 1-oxide (5.41 g, 1 eq) and diacetoxyiodobenzene (12.1 g, 1.5 eq). The reaction mixture was stirred at RT overnight. Then it was filtered through a pad of celite and silica gel, washed with DCM first then with EtOAc. The filtrate was concentrated and the resulting oily residue was taken up in MeOH (250 mL), to which was added potassium carbonate (17.3 g, 5 eq). The reaction mixture was stirred at RT for 2 hours and filtered through a pad of celite and silica gel and washed with MeOH. The filtrate was concentrated under reduced pressure and the resulting lightly brown oily residue was treated with EtOAc with stirring at RT. The mixture was filtered again and the filtrate was concentrated yielding the title compound as a crude light brown soft solid which was used directly without further purification.

$^1$H NMR (DMSO-d$_6$) δ: 3.84 (ddd, J=14.4, 4.5, 4.4 Hz, 2H), 3.79 (s, 1H), 3.49-3.58 (m, 2H), 2.96 (t, J=4.3 Hz, 4H), 1.41 (s, 9H)

Example 1

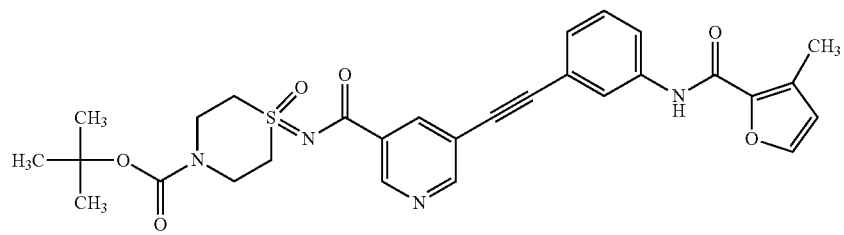 [SMILES: Cc1ccoc1C(=O)Nc1cccc(C#Cc2cncc(C(=O)N=S3(=O)CCN(C(=O)OC(C)(C)C)CC3)c2)c1]

tert-Butyl 1-({[5-({3-[(3-methyl-2-furoyl)amino]phenyl}ethynyl)pyridin-3-yl]carbony}imino)-1λ⁴,4-thiazinane-4-carboxylate 1-oxide A stirring solution of tert-butyl 1-imino-1λ⁴,4-thiazinane-4-carboxylate 1-oxide, (468 mg, 2 mmol, 1 eq) and 5-{3-[(3-methyl-furan-2-carbonyl)-amino]-phenylethynyl}-nicotinic acid, (730 mg, 1.05 eq) in DMF (7 mL) under nitrogen atmosphere was treated with DIPEA (0.70 mL, 2 eq) and BOP (1.0 g, 1.1 eq). The resulting reaction mixture was stirred at RT for 15 minutes and then diluted with EtOAc. The mixture was washed sequentially with saturated aq NaHCO₃ (2×), aq NH₄Cl (1×), and brine (1×), and then dried with anhydrous Na₂SO₄ and concentrated. The residue was purified by gradient chromatography (EtOAc-Hex from 1:3 to 1:1) to give the title compound as white foam (820 mg, 73%). ¹H NMR (DMSO-d₆) δ: 10.21 (s, 1H), 9.11 (d, J=2.0 Hz, 1H), 8.93 (d, J=2.0 Hz, 1H), 8.44 (t, J=2.1 Hz, 1H), 8.14 (t, J=1.7 Hz, 1H), 7.77-7.83 (m, 2H), 7.39-7.44 (m, 1H), 7.34 (dt, J=7.8, 1.0 Hz, 1H), 6.61 (d, J=1.2 Hz, 1H), 3.99-4.10 (m, 2H), 3.80-3.86 (m, 2H), 3.55-3.67 (m, 4H), 2.35 (s, 3H), 1.43 (s, 9H)

Example 2

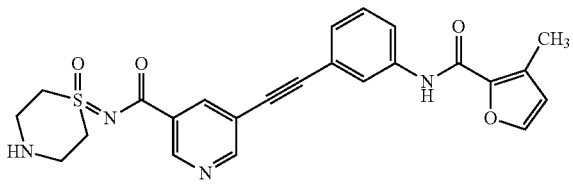 [SMILES: Cc1ccoc1C(=O)Nc1cccc(C#Cc2cncc(C(=O)N=S3(=O)CCNCC3)c2)c1]

5-({3-[(3-Methyl-2-furoyl)amino]phenyl}ethynyl)-N-(1-oxido-1λ⁴,4-thiazinan-1-ylidene)nicotinamide A 0° C. solution of tert-butyl 1-({[5-({3-[(3-methyl-2-furoyl)amino]phenyl}ethynyl)pyridin-3-yl]carbonyl}imino)-1λ⁴,4-thiazinane-4-carboxylate 1-oxide (260 mg, 0.46 mmol, 1 eq) in DCM (2.0 mL) was treated dropwise with trifluoroacetic acid (0.72 mL) and the reaction was stirred at RT for 3 hours. The reaction mixture was diluted with chloroform, washed with saturated aq NaHCO₃ (1×), brine (1×), and dried with anhydrous Na₂SO₄ overnight. The upper clear layer was decanted, concentrated, and the oily residue was purified by column chromatography (MeOH—CHCl₃ 1:100 to 1:25) to give the title compound as white solid (172 mg, 81%). ¹H NMR (DMSO-d₆) δ: 10.21 (s, 1H), 9.11 (d, J=2.0 Hz, 1H), 8.93 (d, J=2.1 Hz, 1H), 8.42 (t, J=2.0 Hz, 1H), 8.13 (t, J=1.7 Hz, 1H), 7.78-7.82 (m, 2H), 7.39-7.43 (m, 1H), 7.34 (dt, J=7.6, 1.2 Hz, 1H), 6.61 (d, J=1.5 Hz, 1H), 3.75 (dt, J=13.9, 2.6 Hz, 2H), 3.33-3.40 (m, 2H), 3.24-3.30 (m, 2H), 3.00-3.09 (m, 2H), 2.35 (s, 3H).

Example 3

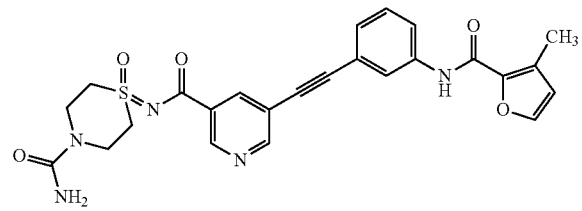 [SMILES: Cc1ccoc1C(=O)Nc1cccc(C#Cc2cncc(C(=O)N=S3(=O)CCN(C(N)=O)CC3)c2)c1]

1-({[5-({3-[(3-Methyl-2-furoyl)amino]phenyl}ethynyl)pyridin-3-yl]carbonyl}imino)-1λ⁴,4-thiazinane-4-carboxamide 1-oxide In a manner similar to that described in Example 5, 5-({3-[(3-methyl-2-furoyl)amino]phenyl}ethynyl)-N-(1-oxido-1λ⁴,4-thiazinan-1-ylidene)nicotinamide and isocyanatotrimethylsilane were converted to the title compound.

¹H NMR (DMSO-d₆) δ: 10.21 (s, 1H), 9.12 (d, J=2.0 Hz, 1H), 8.93 (d, J=2.1 Hz, 1H), 8.44 (t, J=2.1 Hz, 1H), 8.13 (t, J=1.6 Hz, 1H), 7.82 (d, J=1.5 Hz, 1H), 7.78-7.81 (m, 1H), 7.39-7.43 (m, 1H), 7.34 (dt, J=7.7, 1.1 Hz, 1H), 6.61 (d, J=1.5 Hz, 1H), 6.35 (s, 2H), 4.05-4.12 (m, 2H), 3.77-3.83 (m, 2H), 3.56-3.64 (m, 2H), 3.46-3.53 (m, 2H), 2.35 (s, 3H)

Example 4

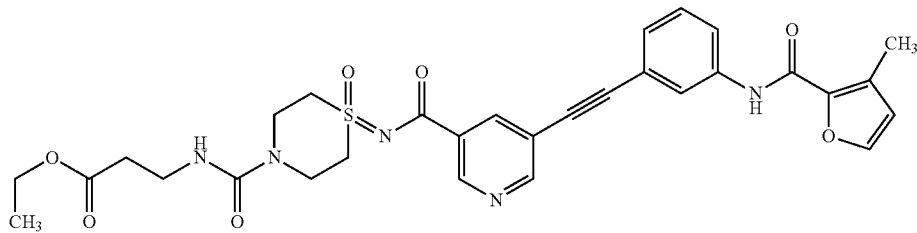 [SMILES: CCOC(=O)CCNC(=O)N1CCS(=O)(=NC(=O)c2cncc(C#Cc3cccc(NC(=O)c4occc4C)c3)c2)CC1]

Ethyl 3-({[1-({[5-({3-[(3-methyl-2-furoyl)amino]phenyl}ethynyl)pyridin-3-yl]carbonyl}imino)-1-oxido-1λ⁴,4-thiazinan-4-yl]carbonyl}amino)propanoate In a manner similar to that described in Example 5, 5-({3-[(3-methyl-2-furoyl)amino]phenyl}ethynyl)-N-(1-oxido-1λ⁴,4-thiazinan-1-ylidene)nicotinamide and ethyl 3-isocyanatopropanoate were converted to the title compound.

¹H NMR (DMSO-d₆) δ: 10.21 (s, 1H), 9.12 (d, J=2.0 Hz, 1H), 8.93 (d, J=2.1 Hz, 1H), 8.44 (t, J=2.0 Hz, 1H), 8.13 (t, J=1.7 Hz, 1H), 7.82 (d, J=1.6 Hz, 1H), 7.78-7.81 (m, 1H), 7.39-7.43 (m, 1H), 7.34 (dt, J=7.6, 1.1 Hz, 1H), 7.02 (t, J=5.3 Hz, 1H), 6.61 (d, J=1.5 Hz, 1H), 4.02-4.10 (m, 4H), 3.77-3.83 (m, 2H), 3.56-3.64 (m, 2H), 3.44-3.51 (m, 2H), 3.26-3.30 (m, 2H), 2.45-2.49 (m, 2H), 2.35 (s, 3H), 1.18 (t, J=7.1 Hz, 3H)

Example 5

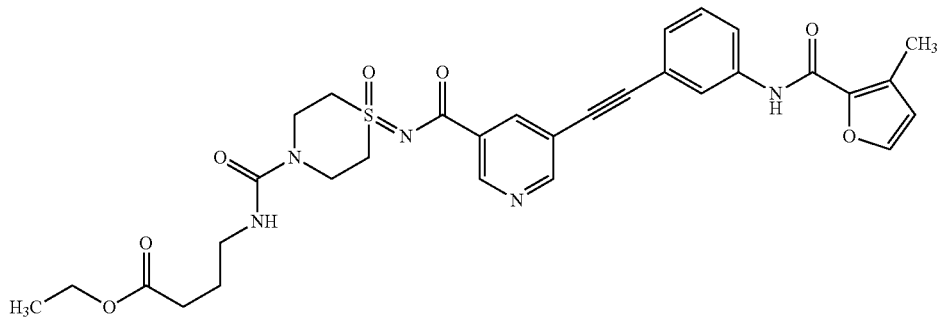 [SMILES: CCOC(=O)CCCNC(=O)N1CCS(=O)(=NC(=O)c2cncc(C#Cc3cccc(NC(=O)c4occc4C)c3)c2)CC1]

Ethyl 4-({[1-({[5-({3[(3-methyl-2-furoyl)amino]phenyl}ethynyl)pyridin-3-yl]carbonyl}imino)-1-oxido-1λ$^4$,4-thiazinan-4-yl]carbonyl}amino)butanoate To a solution of 5-({3-[(3-methyl-2-furoyl)amino]phenyl}ethynyl)-N-(1-oxido-1λ$^4$,4-thiazinan-1-ylidene)nicotinamide_ (Example 2) (170 mg, 0.368 mmol, 1 eq) in DMF (2 mL) was added dropwise ethyl 4-isocyanatobutyrate (179 mg, 3 eq) and the reaction was stirred at RT for 3 hours. The reaction was then poured into saturated aq NaHCO$_3$ and extracted with EtOAc. The organic layer isolated was then washed with aq NH$_4$Cl (1×), brine (1×), and dried with anhydrous Na$_2$SO$_4$ and concentrated. The residue was purified by gradient column chromatography (EtOAc-Hex 3:1 to 6:1) to give the title compound as white solid (196 mg, 86%).

$^1$H NMR (DMSO-d$_6$) δ: 10.21 (s, 1H), 9.12 (d, J=2.1 Hz, 1H), 8.93 (d, J=2.1 Hz, 1H), 8.44 (t, J=2.0 Hz, 1H), 8.13 (t, J=1.7 Hz, 1H), 7.82 (d, J=1.6 Hz, 1H), 7.78-7.81 (m, 1H), 7.39-7.43 (m, 1H), 7.34 (dt, J=7.7, 1.2 Hz, 1H), 6.90 (t, J=5.4 Hz, 1H), 6.61 (d, J=1.6 Hz, 1H), 4.01-4.12 (m, 4H), 3.76-3.83 (m, 2H), 3.62 (dd, J=13.1, 9.4 Hz, 2H), 3.46-3.53 (m, 2H), 3.04-3.09 (m, 2H), 2.35 (s, 3H), 2.31 (t, J=7.5 Hz, 2H), 1.68 (quin, J=7.2 Hz, 2H), 1.17 (t, J=7.1 Hz, 3H)

Example 6

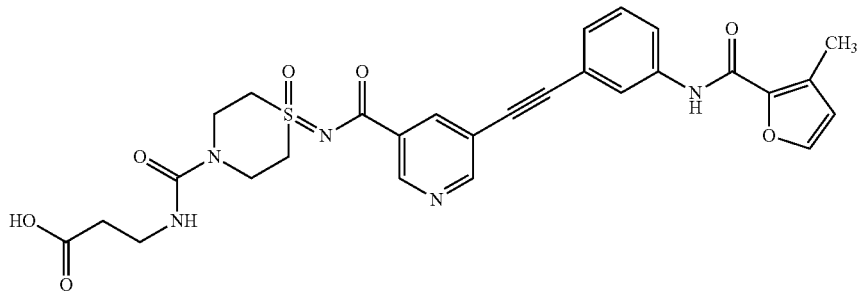 [SMILES: Cc1ccoc1C(=O)Nc1cccc(C#Cc2cncc(C(=O)N=S3(=O)CCN(C(=O)NCCC(=O)O)CC3)c2)c1]

3-({[1-({[5-({3-[(3-Methyl-2-furoyl)amino]phenyl}ethynyl)pyridin-3-yl]carbonyl}imino)-1-oxido-1λ$^4$,4-thiazinan-4-yl]carbonyl}amino)propanoic acid In a manner similar to that described in Example 7, ethyl 3-({[1-({[5-({3-[(3-methyl-2-furoyl)amino]phenyl}ethynyl)pyridin-3-yl]carbonyl}imino)-1-oxido-1λ$^4$,4-thiazinan-4-yl]carbonyl}amino)propanoate was converted to the title compound.

$^1$H NMR (DMSO-d$_6$) δ: 12.09 (br. s., 1H), 10.21 (s, 1H), 9.12 (d, J=2.0 Hz, 1H), 8.93 (d, J=2.1 Hz, 1H), 8.44 (t, J=2.0 Hz, 1H), 8.13 (t, J=1.6 Hz, 1H), 7.77-7.83 (m, 2H), 7.39-7.43 (m, 1H), 7.34 (d, J=7.7 Hz, 1H), 7.00 (t, J=5.0 Hz, 1H), 6.61 (d, J=1.6 Hz, 1H), 4.04-4.11 (m, 2H), 3.76-3.83 (m, 2H), 3.56-3.64 (m, 2H), 3.44-3.52 (m, 2H), 3.23-3.29 (m, 2H), 2.40 (t, J=7.0 Hz, 2H), 2.35 (s, 3H)

Example 7

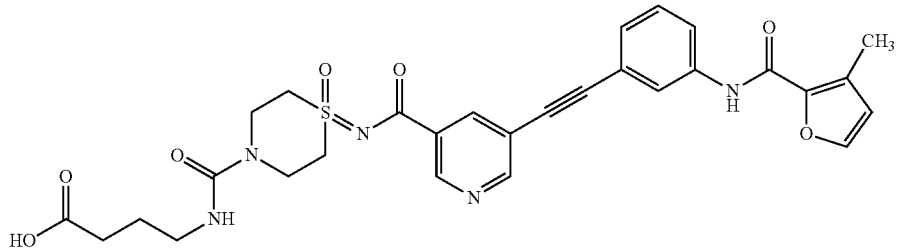 [SMILES: Cc1ccoc1C(=O)Nc1cccc(C#Cc2cncc(C(=O)N=S3(=O)CCN(C(=O)NCCCC(=O)O)CC3)c2)c1]

4-({[1-({[5-({3-[(3-Methyl-2-furoyl)amino]phenyl}ethynyl)pyridin-3-yl]carbonyl}imino)-1-oxido-1λ⁴,4-thiazinan-4-yl]carbonyl}amino)butanoic acid A solution of ethyl 4-({[1-({[5-({3-[(3-methyl-2-furoyl)amino]phenyl}ethynyl)pyridin-3-yl]carbonyl}imino)-1-oxido-1λ⁴,4-thiazinan-4-yl]carbonyl}amino)butanoate (Example 5) (182 mg, 0.294 mmol, 1 eq) in THF (4 mL) was treatd with 1 N KOH (1.5 mL) dropwise and the reaction was stirred at RT for 3 hours. The reaction was cooled to 0° C. and 2N aq HCl (0.6 mL) was added dropwise. The resulting mixture was partitioned between aq NH₄Cl and EtOAc. The organic layer was isolated, washed with brine (1×), and dried over anhydrous Na₂SO₄. The clear upper solution was decanted, concentrated. The resiude was purified by column chromatography (MeOH-DCM 1:20 to 1:10) to give the title compound as white solid (148 mg, 77%).

¹H NMR (DMSO-d₆) δ: 12.00 (br. s., 1H), 10.21 (s, 1H), 9.12 (d, J=2.1 Hz, 1H), 8.93 (d, J=2.1 Hz, 1H), 8.44 (t, J=2.0 Hz, 1H), 8.13 (dt, J=6.8, 1.6 Hz, 1H), 7.78-7.83 (m, 2H), 7.39-7.44 (m, 1H), 7.34 (dd, J=7.6, 1.2 Hz, 1H), 6.90 (t, J=5.3 Hz, 1H), 6.61 (d, J=1.1 Hz, 1H), 4.05-4.13 (m, 2H), 3.77-3.84 (m, 2H), 3.57-3.65 (m, 2H), 3.45-3.52 (m, 2H), 3.03-3.09 (m, 2H), 2.35 (s, 3H), 2.23 (t, J=7.3 Hz, 2H), 1.66 (quin, J=7.2 Hz, 2H).

Example 8

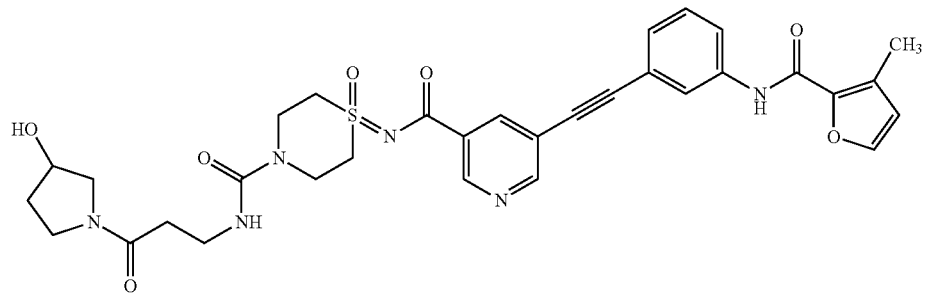 [SMILES: Cc1ccoc1C(=O)Nc1cccc(C#Cc2cncc(C(=O)N=S3(=O)CCN(C(=O)NCCC(=O)N4CCC(O)C4)CC3)c2)c1]

N-[3-(3-Hydroxypyrrolidin-1-yl)-3-oxopropyl]-1-({[5-({3-[(3-methyl-2-furoyl)amino]phenyl}ethynyl)pyridin-3-yl]carbonyl}imino)-1λ⁴,4-thiazinane-4-carboxamide 1-oxide In a manner similar to that described in Example 9, 3-({[1-({[5-({3-[(3-methyl-2-furoyl)amino]phenyl}ethynyl)pyridin-3-yl]carbonyl}imino)-1-oxido-1λ⁴,4-thiazinan-4-yl]carbonyl}propanoic acid and DL-pyrrolidin-3-ol were converted to the title compound.

¹H NMR (DMSO-d₆) δ: 10.21 (s, 1H), 9.12 (d, J=2.0 Hz, 1H), 8.93 (d, J=2.1 Hz, 1H), 8.44 (t, J=2.1 Hz, 1H), 8.13 (t, J=1.6 Hz, 1H), 7.82 (d, J=1.5 Hz, 1H), 7.78-7.81 (m, 1H), 7.39-7.43 (m, 1H), 7.34 (dt, J=7.6, 1.1 Hz, 1H), 6.96 (t, J=5.3 Hz, 1H), 6.61 (d, J=1.3 Hz, 1H), 4.88-4.99 (m, 1H), 4.20-4.31 (m, 1H), 4.07 (dd, J=16.0, 2.8 Hz, 2H), 3.77-3.83 (m, 2H), 3.60 (dd, J=13.9, 9.0 Hz, 2H), 3.36-3.52 (m, 4H), 3.21-3.29 (m, 4H), 2.37-2.46 (m, 2H), 2.35 (s, 3H), 1.72-1.96 (m, 2H)

Example 9

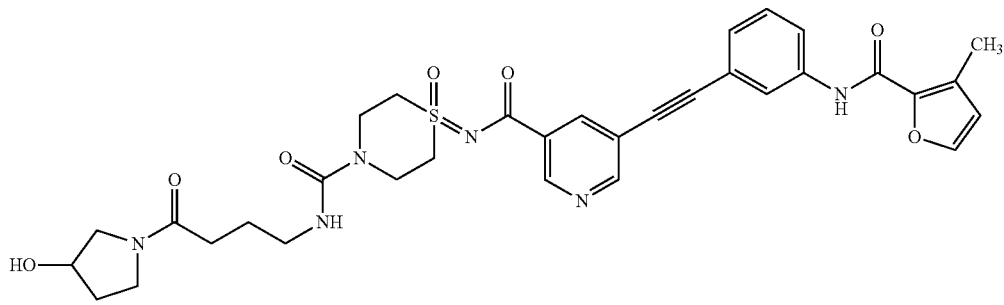 [SMILES: Cc1ccoc1C(=O)Nc1cccc(C#Cc2cncc(C(=O)N=S3(=O)CCN(C(=O)NCCCC(=O)N4CCC(O)C4)CC3)c2)c1]

N-[4-(3-Hydroxypyrrolidin-1-yl)-4-oxobutyl]-1-({[5-({3-[(3-methyl-2-furoyl)amino]phenyl}ethynyl)pyridin-3-yl]carbonyl}imino)-1λ⁴,4-thiazinane-4-carboxamide 1-oxide A solution of 4-({[1-({[5-({3-[(3-methyl-2-furoyl)amino]phenyl}ethynyl)pyridin-3-yl]carbonyl}imino)-1-oxido-1λ⁴,4-thiazinan-4-yl]carbonyl}butanoic acid (Example 7) (65 mg, 0.11 mmol, 1 eq) and DL-3-pyrrolidinol (43.6 mg, 5 eq) in DMF (1 mL) at 0° C. was treated with 1-hydroxybenzotriazole hydrate (25.2 mg, 1.5 eq), DIPEA (0.14 mL, 7 eq), and BOP (73 mg, 1.5 eq). The reaction mixture was stirred at 0° C. for 30 minutes, and it was then poured into aq NH₄Cl. The reaction mixture was extracted with EtOAc. The organic layer was washed with a combination of saturated aq NaHCO₃ and brine (1×), brine (1×), and lastly dried with anhydrous Na₂SO₄. The residue was purified by gradient column chromatography (from neat EtOAc to MeOH-EtOAc 1:5) to give the title compound as white solid (39 mg, 53%).

¹H NMR (DMSO-d₆) δ: 10.21 (s, 1H), 9.12 (d, J=2.0 Hz, 1H), 8.93 (d, J=2.2 Hz, 1H), 8.44 (t, J=2.1 Hz, 1H), 8.13 (t, J=1.6 Hz, 1H), 7.78-7.83 (m, 2H), 7.39-7.43 (m, 1H), 7.34 (dt, J=7.6, 1.1 Hz, 1H), 6.91 (t, J=4.9 Hz, 1H), 6.61 (d, J=1.5 Hz, 1H), 4.87-4.98 (m, 1H), 4.20-4.31 (m, 1H), 4.09 (d, J=16.1 Hz, 2H), 3.77-3.82 (m, 2H), 3.62 (dd, J=13.6, 9.4 Hz, 2H), 3.35-3.52 (m, 4H), 3.20-3.30 (m, 2H), 3.07 (q, J=5.9 Hz, 2H), 2.35 (s, 3H), 2.18-2.28 (m, 2H), 1.63-1.93 (m, 4H).

Example 10

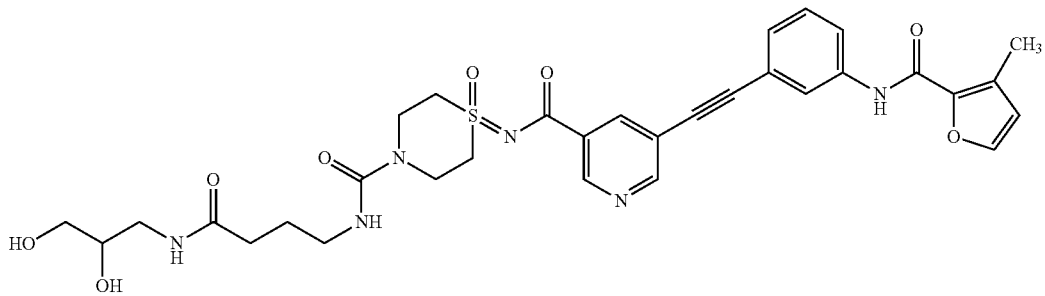 [SMILES: Cc1ccoc1C(=O)Nc1cccc(C#Cc2cncc(C(=O)N=S3(=O)CCN(C(=O)NCCCC(=O)NCC(O)CO)CC3)c2)c1]

N-{4-[(2,3-Dihydroxypropyl)amino]-4-oxobutyl}-1-({[5-({3-[(3-methyl-2-furoyl)amino]phenyl}ethynyl)pyridin-3-yl]carbonyl}imino)-1λ⁴,4-thiazinane-4-carboxamide 1-oxide In a manner similar to that described in Example 9, a solution of 4-({[1-({[5-({3-[(3-methyl-2-furoyl)amino]phenyl}ethynyl)pyridin-3-yl]carbonyl}imino)-1-oxido-1λ⁴,4-thiazinan-4-yl]carbonyl}amino)butanoic acid and 3-aminopropane-1,2-diol were converted to the title compound.

¹H NMR (DMSO-d₆) δ: 10.21 (s, 1H), 9.12 (d, J=2.0 Hz, 1H), 8.93 (d, J=2.2 Hz, 1H), 8.44 (t, J=2.1 Hz, 1H), 8.13 (t, J=1.6 Hz, 1H), 7.76-7.83 (m, 3H), 7.39-7.43 (m, 1H), 7.34 (d, J=7.8 Hz, 1H), 6.90 (t, J=5.1 Hz, 1H), 6.61 (d, J=1.5 Hz, 1H), 4.72 (d, J=4.9 Hz, 1H), 4.50 (t, J=5.9 Hz, 1H), 4.06-4.12 (m, 2H), 3.77-3.83 (m, 2H), 3.61 (dd, J=13.4, 9.8 Hz, 2H), 3.44-3.52 (m, 3H), 3.26 (dtd, J=10.5, 5.5, 5.3 Hz, 2H), 3.18 (ddd, J=13.3, 5.6, 5.5 Hz, 1H), 3.01-3.07 (m, 2H), 2.93-2.99 (m, 1H), 2.35 (s, 3H), 2.11 (t, J=7.5 Hz, 2H), 1.65 (dt, J=14.5, 7.3 Hz, 2H)

Example 11

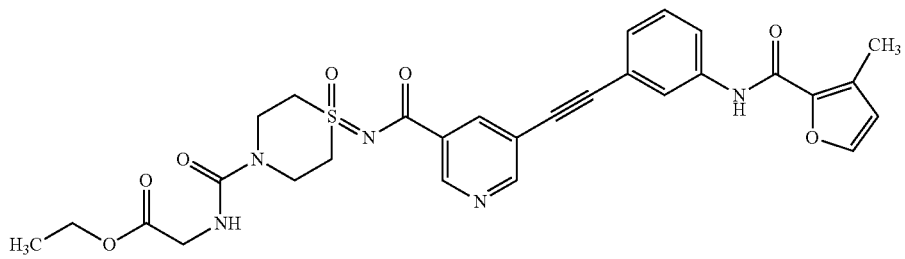 [SMILES: CCOC(=O)CNC(=O)N1CCS(=O)(=NC(=O)c2cncc(C#Cc3cccc(NC(=O)c4occc4C)c3)c2)CC1]

Ethyl({[1-({[5-({3-[(3-methyl-2-furoyl)amino]phenyl}ethynyl)pyridin-3-yl]carbonyl}imino)-1-oxido-1λ⁴,4-thiazinan-4-yl]carbonyl}amino)acetate In a manner similar to that described in Example 5, 5-({3-[(3-methyl-2-furoyl)amino]phenyl}ethynyl)-N-(1-oxido-1λ⁴,4-thiazinan-1-ylidene)nicotinamide and ethyl 2-isocyanatoacetate were converted to the title compound.

¹H NMR (DMSO-d₆) δ: 10.21 (s, 1H), 9.12 (d, J=2.0 Hz, 1H), 8.93 (d, J=2.1 Hz, 1H), 8.45 (t, J=2.0 Hz, 1H), 8.13 (s, 1H), 7.78-7.83 (m, 2H), 7.39-7.47 (m, 2H), 7.34 (d, J=7.7 Hz, 1H), 6.61 (d, J=1.6 Hz, 1H), 4.05-4.14 (m, 4H), 3.81-3.87 (m, 2H), 3.78 (d, J=5.7 Hz, 2H), 3.65 (dd, J=13.3, 9.7 Hz, 2H), 3.44-3.51 (m, 2H), 2.35 (s, 3H), 1.17-1.21 (m, 3H)

Example 12

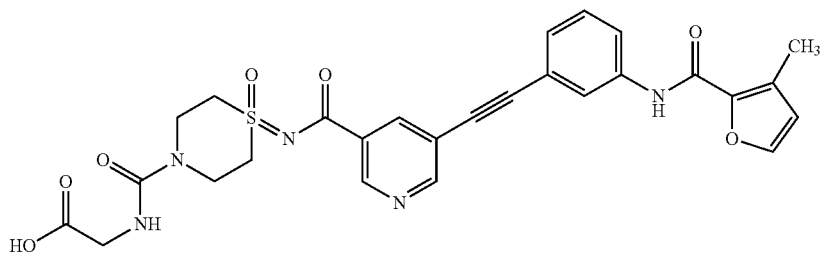 [SMILES: Cc1ccoc1C(=O)Nc1cccc(C#Cc2cncc(C(=O)N=S3(=O)CCN(C(=O)NCC(=O)O)CC3)c2)c1]

({[1-({[5-({3-[(3-Methyl-2-furoyl)amino]phenyl}ethynyl)pyridin-3-yl]carbonyl}imino)-1-oxido-1λ⁴,4-thiazinan-4-yl]carbonyl}amino)acetic acid In a manner similar to that described in Example 7, ethyl ({[1-({[5-({3-[(3-methyl-2-furoyl)amino]phenyl}ethynyl)pyridin-3-yl]carbonyl}imino)-1-oxido-1λ⁴,4-thiazinan-4-yl]carbonyl}amino)acetate is converted to the title compound.

¹H NMR (DMSO-d₆) δ: 10.21 (s, 1H), 9.12 (d, J=2.1 Hz, 1H), 8.93 (d, J=2.1 Hz, 1H), 8.45 (t, J=2.0 Hz, 1H), 8.13 (t, J=1.6 Hz, 1H), 7.82 (d, J=1.5 Hz, 1H), 7.78-7.81 (m, 1H), 7.39-7.43 (m, 1H), 7.34 (dt, J=7.6, 1.1 Hz, 1H), 6.99 (br. s., 1H), 6.61 (d, J=1.5 Hz, 1H), 4.07-4.14 (m, 2H), 3.84 (dd, J=11.6, 2.8 Hz, 2H), 3.62 (dd, J=13.6, 9.9 Hz, 2H), 3.48-3.56 (m, 4H), 2.35 (s, 3H)

Example 13

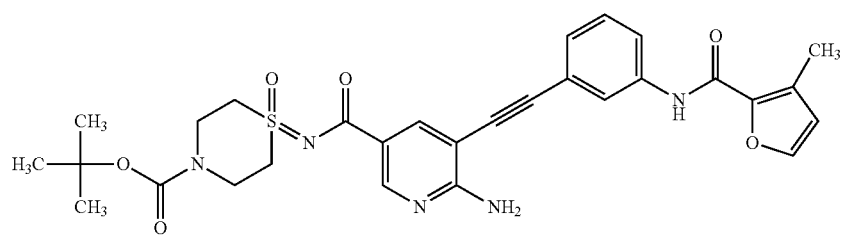 [SMILES: Cc1ccoc1C(=O)Nc1cccc(C#Cc2cc(C(=O)N=S3(=O)CCN(C(=O)OC(C)(C)C)CC3)cnc2N)c1]

tert-Butyl 1-({[6-amino-5-({3-[(3-methyl-2-furoyl)
amino]phenyl}ethynyl)pyridin-3-yl]
carbonyl}imino)-1λ⁴,4-thiazinane-4-carboxylate
1-oxide In a manner similar to that describe in Example 1, tert-butyl 1-imino-1λ⁴,4-thiazinane-4-carboxylate 1-oxide and 6-amino-5-((3-(3-methylfuran-2-carboxamido)phenyl)ethynyl)nicotinic acid are converted to the title compound.

¹H NMR (DMSO-d₆) δ: 10.13 (s, 1H), 8.60 (d, J=1.5 Hz, 1H), 8.09 (s, 2H), 7.81 (s, 1H), 7.74 (d, J=7.6 Hz, 1H), 7.32-7.45 (m, 2H), 7.04 (br. s., 2H), 6.61 (s, 1H), 3.95-4.06 (m, 2H), 3.70-3.82 (m, 2H), 3.46-3.67 (m, 4H), 2.35 (s, 3H), 1.43 (s, 9H

Example 14

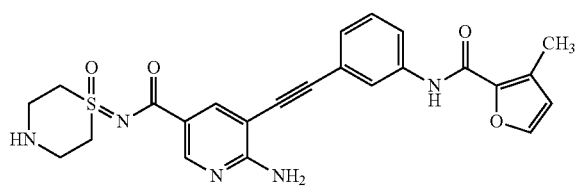 [SMILES: Cc1ccoc1C(=O)Nc1cccc(C#Cc2cc(C(=O)N=S3(=O)CCNCC3)cnc2N)c1]

6-Amino-5-({3-[(3-methyl-2-furoyl)amino]
phenyl}ethynyl)-N-(1-oxido-1λ⁴,4-thiazinan-1-
ylidene)nicotinamide In a manner similar to that described in Example 2, tert-butyl 1-({[6-amino-5-({3-[(3-methyl-2-furoyl)amino]phenyl}ethynyl)pyridin-3-yl]carbonyl}imino)-1λ⁴,4-thiazinane-4-carboxylate 1-oxide was converted to the title compound.

¹H NMR (DMSO-d₆) δ: 10.13 (s, 1H), 8.59 (d, J=2.3 Hz, 1H), 8.08 (t, J=1.8 Hz, 2H), 7.81 (d, J=1.6 Hz, 1H), 7.74 (ddd, J=8.4, 1.5, 1.2 Hz, 1H), 7.40-7.44 (m, 1H), 7.34-7.39 (m, 1H), 7.01 (br. s., 2H), 6.61 (d, J=1.6 Hz, 1H), 3.68 (dt, J=13.6, 2.4 Hz, 2H), 3.19-3.30 (m, 4H), 2.96-3.04 (m, 2H), 2.42-2.47 (m, 1H), 2.35 (s, 3H)

Example 15

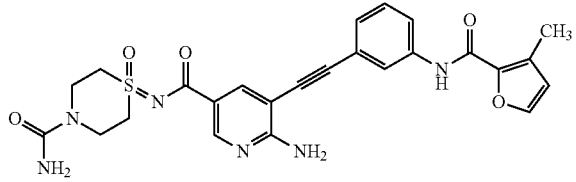 [SMILES: Cc1ccoc1C(=O)Nc1cccc(C#Cc2cc(C(=O)N=S3(=O)CCN(C(N)=O)CC3)cnc2N)c1]

1-({[6-Amino-5-({3-[(3-methyl-2-furoyl)amino]
phenyl}ethynyl)pyridin-3-yl]carbonyl}imino)-1λ⁴,4-
thiazinane-4-carboxamide 1-oxide In a manner similar to that described in Example 5, 6-amino-5-({3-[(3-methyl-2-furoyl)amino]phenyl}ethynyl)-N-(1-oxido-1λ⁴,4-thiazinan-1-ylidene)nicotinamide and isocyanatotrimethylsilane were converted to the title compound.

¹H NMR (DMSO-d₆) δ: 10.13 (s, 1H), 8.60 (d, J=2.2 Hz, 1H), 8.08-8.11 (m, 2H), 7.81 (d, J=1.2 Hz, 1H), 7.74 (d, J=7.8 Hz, 1H), 7.40-7.44 (m, 1H), 7.34-7.39 (m, 1H), 7.03 (br. s., 2H), 6.61 (d, J=1.5 Hz, 1H), 6.33 (s, 2H), 4.00-4.07 (m, 2H), 3.70-3.77 (m, 2H), 3.52-3.60 (m, 2H), 3.37-3.45 (m, 2H), 2.35 (s, 3H)

Example 16

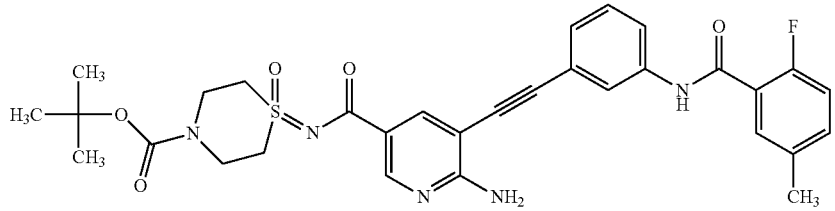 [SMILES: Cc1ccc(F)c(C(=O)Nc2cccc(C#Cc3cc(C(=O)N=S4(=O)CCN(C(=O)OC(C)(C)C)CC4)cnc3N)c2)c1]

tert-butyl 1-({[6-Amino-5-({3-[(2-fluoro-5-methyl-
benzoyl)amino]phenyl}ethynyl)pyridin-3-yl]
carbonyl}imino)-1λ⁴,4-thiazinane-4-carboxylate
1-oxide In a manner similar to that describe in Example 1, tert-butyl 1-imino-1λ⁴,4-thiazinane-4-carboxylate 1-oxide and 6-amino-5-((3-2-fluoro-5-methylbenzamido)phenyl)ethynyl)nicotinic acid are converted to the title compound.

¹H NMR (DMSO-d₆) δ: 10.46 (s, 1H), 8.60 (d, J=2.2 Hz, 1H), 8.09 (d, J=2.2 Hz, 1H), 8.02 (s, 1H), 7.68 (d, J=7.9 Hz, 1H), 7.43-7.50 (m, 2H), 7.36-7.42 (m, 2H), 7.22-7.26 (m, 1H), 7.05 (br. s., 2H), 3.97-4.01 (m, 2H), 3.73-3.79 (m, 2H), 3.61 (br. s., 2H), 3.48-3.55 (m, 2H), 2.35 (s, 3H), 1.42 (s, 9H)

Example 17

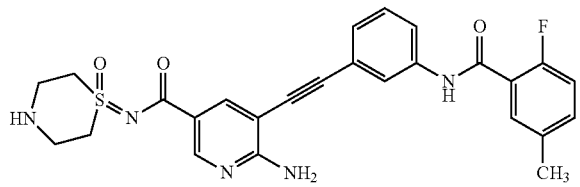 [SMILES: Cc1ccc(F)c(C(=O)Nc2cccc(C#Cc3cc(C(=O)N=S4(=O)CCNCC4)cnc3N)c2)c1]

6-Amino-5-({3-[(2-fluoro-5-methylbenzoyl)amino]phenyl}ethynyl)-N-(1-oxido-1λ⁴,4-thiazinan-1-ylidene)nicotinamide In a manner similar to that described in Example 2, tert-butyl 1-({[6-amino-5-({3-[(2-fluoro-5-methylbenzoyl)amino]phenyl}ethynyl)pyridin-3-yl]carbonyl}imino)-1λ⁴,4-thiazinane-4-carboxylate 1-oxide is converted to the title compound.

$^1$H NMR (DMSO-d$_6$) δ: 10.46 (s, 1H), 8.59 (d, J=2.2 Hz, 1H), 8.08 (d, J=2.2 Hz, 1H), 8.02 (s, 1H), 7.68 (d, J=7.9 Hz, 1H), 7.48 (dd, J=6.6, 1.6 Hz, 1H), 7.44-7.46 (m, 1H), 7.36-7.42 (m, 2H), 7.22-7.26 (m, 1H), 7.03 (br. s., 2H), 3.68 (ddd, J=13.7, 2.5, 2.3 Hz, 2H), 3.21-3.31 (m, 4H), 3.01 (ddd, J=13.6, 9.0, 1.8 Hz, 2H), 2.57 (br. s., 1H), 2.35 (s, 3H)

Example 18

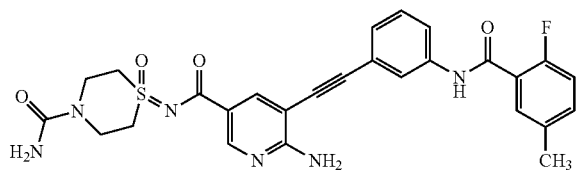

1-({[6-Amino-5-({3-[(2-fluoro-5-methylbenzoyl)amino]phenyl}ethynyl)pyridin-3-yl]carbonyl}imino)-1λ⁴,4-thiazinane-4-carboxamide 1-oxide In a manner similar to that described in Example 5, 6-amino-5-({3-[(2-fluoro-5-methylbenzoyl)amino]phenyl}ethynyl)-N-(1-oxido-1λ⁴,4-thiazinan-1-ylidene)nicotinamide and isocyanatotrimethylsilane are converted to the title compound.

$^1$H NMR (DMSO-d$_6$) δ: 10.46 (s, 1H), 8.60 (d, J=2.2 Hz, 1H), 8.10 (d, J=2.2 Hz, 1H), 8.02 (s, 1H), 7.68 (d, J=7.9 Hz, 1H), 7.48 (dd, J=6.7, 1.8 Hz, 1H), 7.44-7.47 (m, 1H), 7.36-7.42 (m, 2H), 7.24 (dd, J=9.9, 8.7 Hz, 1H), 7.04 (br. s., 2H), 6.32 (s, 2H), 4.00-4.06 (m, 2H), 3.71-3.76 (m, 2H), 3.57 (dd, J=13.1, 9.2 Hz, 2H), 3.38-3.44 (m, 2H), 2.35 (s, 3H)

Example 19

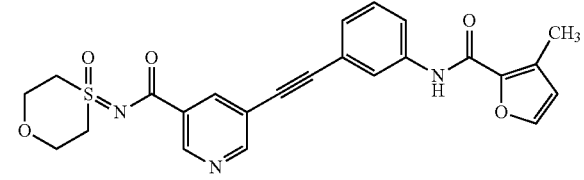 [SMILES: Cc1ccoc1C(=O)Nc1cccc(C#Cc2cncc(C(=O)N=S3(=O)CCOCC3)c2)c1]

5-({3-[(3-methyl-2-furoyl)amino]phenyl}ethynyl)-N-(4-oxido-1,4λ⁴-oxathian-4-ylidene)nicotinamide In a manner similar to that described herein, 5-iodo-N-(4-oxido-1,4λ⁴-oxathian-4-ylidene)nicotinamide and 3-methyl-furan-2-carboxylic acid (3-ethynyl-phenyl)-amide were converted to the title compound.

$^1$H NMR (DMSO-d$_6$) δ: 10.21 (s, 1H), 9.13 (d, J=2.1 Hz, 1H), 8.94 (d, J=2.1 Hz, 1H), 8.44 (t, J=2.1 Hz, 1H), 8.13 (t, J=1.8 Hz, 1H), 7.82 (d, J=1.5 Hz, 1H), 7.78-7.81 (m, 1H), 7.40-7.43 (m, 1H), 7.34 (dt, J=7.6, 1.2 Hz, 1H), 6.61 (d, J=1.5 Hz, 1H), 4.16-4.20 (m, 2H), 3.96-4.00 (m, 2H), 3.91 (dt, J=14.2, 2.6 Hz, 2H), 3.65-3.70 (m, 2H), 2.35 (s, 3H)

Preparation 4

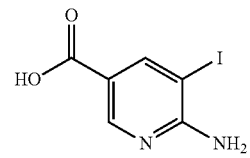

6-Amino-5-iodonicotinic acid

A mixture of methyl 6-amino-5-iodonicotinate, (2.78 g, 10 mmol, 1 eq) and potassium hydroxide (2.8 g, 5 eq) in THF/H$_2$O (120 mL, 3:1) was heated at 50° C. for 48 hours. The reaction was then cooled to room temperature and concentrated HCl was drop wise added until a pH around 3-4 was achieved. The solution was concentrated and the resulting precipitate was collected by filtration to give the title compound as a slightly brown solid (1.77 g.)

$^1$H NMR (DMSO-d$_6$) δ: 12.64 (br. s., 1H), 8.47 (d, J=2.1 Hz, 1H), 8.25 (d, J=1.8 Hz, 1H), 6.88 (br. s., 2H)

Preparation 5

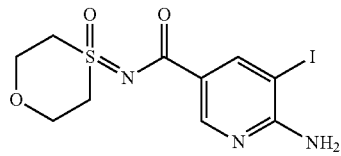 [SMILES: Nc1ncc(C(=O)N=S2(=O)CCOCC2)cc1I]

6-amino-5-iodo-N-(4-oxido-1,4λ⁴-oxathian-4-ylidene)nicotinamide

To a solution of 1,4-oxathiane (510 mg, 3.21 mmol, 1.05 eq) in anhydrous DMF (8 mL) was added 6-amino-5-iodonicotinic acid (806 mg, 1.0 eq), diisopropylethylamine (1.1 mL, 2 eq), and BOP (1.484 g, 1.1 eq). The reaction mixture was heated at 60° C. for 20 hours and then partitioned between EtOAc and aq NH₄Cl. The organic layer was separated, washed further with saturated aq NaHCO₃ (1×), brine (1×), and dried with anhydrous Na₂SO₄ overnight. The upper solution layer was decanted, concentrated, and the brown oily reside was subject to column chromatography (EtOAc-Hex 1:5 to 3:1). Concentration of the product eluting fractions gave the title compound as white solid (889 mg, 77%).

$^1$H NMR (DMSO-d$_6$) δ: 8.57 (d, J=2.1 Hz, 1H), 8.35 (d, J=2.1 Hz, 1H), 6.78 (br. s., 2H), 4.10-4.15 (m, 2H), 3.91 (ddd, J=12.6, 8.5, 2.1 Hz, 2H), 3.79-3.84 (m, 2H), 3.55-3.60 (m, 2H)

Example 20

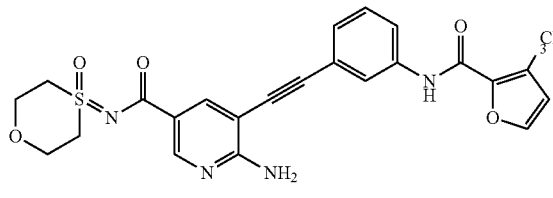

6-amino-5-({3-[(3-methyl-2-furoyl)amino]phenyl}ethynyl)-N-(4-oxido-1,4λ$^4$-oxathian-4-ylidene)nicotinamide To a solution of 6-amino-5-iodo-N-(4-oxido-1,4λ$^4$-oxathian-4-ylidene)nicotinamide (57.2 mg, 0.15 mmol, 1.0 eq) and 3-methyl-furan-2-carboxylic acid (3-ethynyl-phenyl)-amide (43.9 mg, 1.3 eq) in anhydrous DMF (1 mL) under nitrogen atmosphere was added bis(triphenylphosphine)palladium(II) dichloride (10.5 mg, 0.1 eq), triethylamine (0.11 mL, 5.0 eq), and copper(I) iodide (5.7 mg, 0.2 eq). The reaction mixture was stirred at RT for 15 minutes and then partitioned between saturated aq NaHCO₃ and EtOAc. The organic layer was isolated, washed further with aqueous NH₄Cl brine, and dried with anhydrous Na₂SO₄. The organic phase was decanted, dried and concentrated. The residue was subject to a gradient chromatography (EtOAc-Hexanes from 1:9 to neat EtOAc). Concentration of the product eluting fractions gave the title compound as white solid (56 mg).

$^1$H NMR (DMSO-d$_6$) δ: 10.13 (s, 1H), 8.61 (d, J=2.1 Hz, 1H), 8.08-8.10 (m, 2H), 7.81 (d, J=1.8 Hz, 1H), 7.72-7.75 (m, 1H), 7.41-7.43 (m, 1H), 7.35-7.39 (m, 1H), 7.04 (br. s., 2H), 6.60 (d, J=1.5 Hz, 1H), 4.12-4.17 (m, 2H), 3.93 (ddd, J=12.5, 8.7, 2.1 Hz, 2H), 3.82-3.86 (m, 2H), 3.56-3.61 (m, 2H), 2.35 (s, 3H)

Example 21

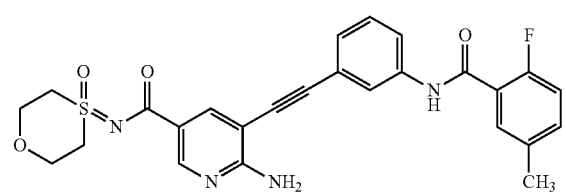 [SMILES: Cc1ccc(F)c(C(=O)Nc2cccc(C#Cc3cc(C(=O)N=S4(=O)CCOCC4)cnc3N)c2)c1]

6-amino-5-({3-[(2-fluoro-5-methylbenzoyl)amino]phenyl}ethynyl)-N-(4-oxido-1,4λ$^4$-oxathian-4-ylidene)nicotinamide In a manner similar to that described in the examples above, 6-amino-5-iodo-N-(4-oxido-1,4λ$^4$-oxathian-4-ylidene)nicotinamide and N-(3-ethynylphenyl)-2-fluoro-5-methylbenzamide were converted to the title compound.

$^1$H NMR (DMSO-d$_6$) δ: 10.46 (s, 1H), 8.61 (d, J=2.1 Hz, 1H), 8.10 (d, J=2.1 Hz, 1H), 8.03 (s, 1H), 7.68 (d, J=8.2 Hz, 1H), 7.44-7.49 (m, 2H), 7.36-7.42 (m, 2H), 7.24 (dd, J=9.8, 8.7 Hz, 1H), 7.06 (br. s., 2H), 4.12-4.16 (m, 2H), 3.93 (ddd, J=12.5, 8.7, 1.9 Hz, 2H), 3.81-3.86 (m, 2H), 3.56-3.61 (m, 2H), 2.35 (s, 3H)

Example 22

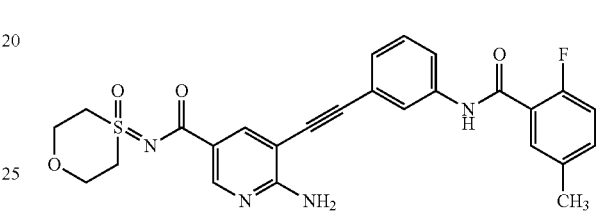

6-amino-5-[(3-{[(2-fluoro-5-methylphenyl)amino]carbonyl}phenyl)ethynyl]-N-(4-oxido-1,4λ$^4$-oxathian-4-ylidene)nicotinamide In a manner similar to that described in the examples above, 6-amino-5-iodo-N-(4-oxido-1,4λ$^4$-oxathian-4-ylidene)nicotinamide and 3-ethynyl-N-(2-fluoro-5-methylphenyl)benzamide were converted to the title compound.

$^1$H NMR (DMSO-d$_6$) δ: 10.15 (s, 1H), 8.62 (d, J=2.3 Hz, 1H), 8.27 (s, 1H), 8.12 (d, J=2.3 Hz, 1H), 7.96 (d, J=7.6 Hz, 1H), 7.91 (d, J=7.9 Hz, 1H), 7.58 (t, J=7.8 Hz, 1H), 7.41 (dd, J=7.3, 1.5 Hz, 1H), 7.18 (dd, J=10.1, 8.7 Hz, 1H), 7.14 (br. s., 2H), 7.06-7.09 (m, 1H), 4.12-4.17 (m, 2H), 3.91-3.96 (m, 2H), 3.83 (ddd, J=14.2, 2.6, 2.3 Hz, 2H), 3.57-3.62 (m, 2H), 2.31 (s, 3H)

Preparation 6

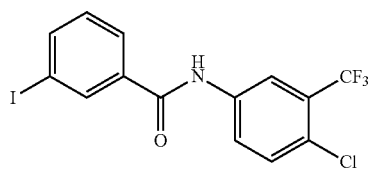 [SMILES: O=C(Nc1ccc(Cl)c(C(F)(F)F)c1)c1cccc(I)c1]

N-[4-chloro-3-(trifluoromethyl)phenyl]-3-iodobenzamide

To the mixture of 3-iodobenzoic acid (1.28 g, 5.04 mmol, 1 eq) and 4-chloro-3-(trifluoromethyl)-aniline (1.48 g, 1.5 eq) in anhydrous DMF (15 mL) was added catalytic amount of DMAP (123.1 mg, 0.2 eq) and EDCI (1.16 g, 1.2 eq). The reaction was stirred at 70° C. for 20 hours. It was then partitioned between EtOAc and saturated aq NaHCO₃. The organic layer was further washed with aqueous NH4Cl brine and dried with anhydrous sodium sulfate. The organic layer was decanted, dried and concentrated. The residue was subject to a gradient column chromatography (from neat Hex to EtOAc-Hex 1:25). The product fractions were collected, concentrated, and the solid residue was triturated with EtOAc-Hex (1:25) and the solid which formed was collected and dried to give that title compound as a white solid (1.996 g, 93%).

$^1$H NMR (DMSO-$d_6$) δ: 10.68 (s, 1H), 8.31-8.34 (m, 2H), 8.10 (dd, J=8.8, 2.3 Hz, 1H), 7.96-8.00 (m, 2H), 7.73 (d, J=8.8 Hz, 1H), 7.37 (t, J=7.8 Hz, 1H)

Preparation 7

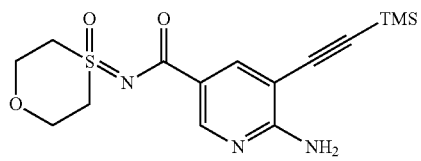 [SMILES: C[Si](C)(C)C#Cc1cc(C(=O)N=S2(=O)CCOCC2)cnc1N]

6-amino-N-(4-oxido-1,4λ$^4$-oxathian-4-ylidene)-5-[(trimethylsilyl)ethynyl]nicotinamide To a reaction vessel containing 6-amino-5-iodo-N-(4-oxido-1,4λ$^4$-oxathian-4-ylidene)nicotinamide, (570 mg, 1.50 mmol, 1 eq) and trimethylsilylacetylene (1.24 mL, 6 eq) in anhydrous DMF (4 mL) under anhydrous nitrogen atmosphere was added triethylamine (1.67 mL, 8 eq), bis(triphenylphosphine)palladium(II) dichloride (105 mg, 0.1 eq), and copper(I) iodide (57.1 mg, 0.2 eq). The reaction mixture was stirred at room temperature for 15 minutes and then partitioned between saturated aq NaHCO$_3$ and EtOAc. The organic layer was separated, washed with aq NH$_4$Cl (1×) and brine (1×), followed by drying with anhydrous Na$_2$SO$_4$. The organic phase was decanted, concentrated, and the brown oily residue was subject to a gradient column chromatography (EtOAc-Hex 1:10 to 5:1). Concentration of the product eluting fractions gave the title compound as white foam (525 mg).

Example 23

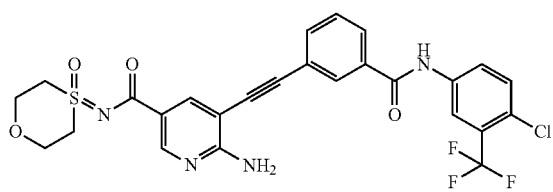 [SMILES: Nc1ncc(C(=O)N=S2(=O)CCOCC2)cc1C#Cc1cccc(C(=O)Nc2ccc(Cl)c(C(F)(F)F)c2)c1]

6-amino-5-{[3-({[4-chloro-3-(trifluoromethyl)phenyl]amino}carbonyl)phenyl]ethynyl}-N-(4-oxido-1,4λ$^4$-oxathian-4-ylidene)nicotinamide To 6-amino-N-(4-oxido-1,4λ$^4$-oxathian-4-ylidene)-5-[(trimethylsilyl)ethynyl]nicotinamide, (71 mg, 0.2 mmol, 1 eq) and N-[4-chloro-3-(trifluoromethyl)phenyl]-3-iodobenzamide (112 mg, 1.3 eq) in anhydrous DMF (2 mL) under nitrogen atmosphere were added copper(I) iodide (8.0 mg, 0.2 eq), triethylamine (0.14 mL, 5 eq), and bis(triphenylphosphine)palladium(II) dichloride (14 mg, 0.1 eq), followed by the final addition of tetrabutylammonium fluoride (1.0 M in THF; 0.22 mL, 1.1 eq). The reaction was stirred at ambient temperature for 15 minutes. Then it was partitioned between EtOAc and aq NH$_4$Cl. The organic layer was isolated, washed with saturated aq NaHCO$_3$, and brine, and dried with anhydrous Na$_2$SO$_4$. The organic layer was decanted, dried and concentrated. The residue was subject to a gradient column chromatography (EtOAc-Hex 1:5 to 1:2) which was followed by another gradient column chromatography (from neat CHCl$_3$ to MeOH—CHCl$_3$ 1:50). The product fractions were collected, concentrated. The solid which formed while concentrating was collected by filtration and dried to give the title compound as a yellow solid (58 mg).

$^1$H NMR (DMSO-$d_6$) δ: 10.73 (s, 1H), 8.63 (d, J=2.3 Hz, 1H), 8.37 (d, J=2.6 Hz, 1H), 8.29 (t, J=1.5 Hz, 1H), 8.11-8.15 (m, 2H), 7.95 (dd, J=16.9, 7.8 Hz, 2H), 7.74 (d, J=8.8 Hz, 1H), 7.61 (t, J=7.8 Hz, 1H), 7.15 (br. s., 2H), 4.12-4.17 (m, 2H), 3.91-3.96 (m, 2H), 3.83 (dt, J=14.3, 2.7 Hz, 2H), 3.57-3.62 (m, 2H)

Example 24

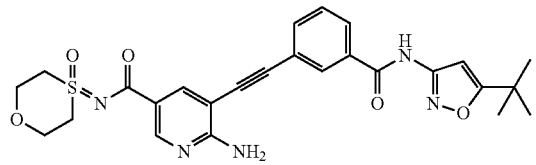 [SMILES: CC(C)(C)c1cc(NC(=O)c2cccc(C#Cc3cc(C(=O)N=S4(=O)CCOCC4)cnc3N)c2)no1]

6-amino-5-[(3-{[(5-tert-butylisoxazol-3-yl)amino]carbonyl}phenyl)ethynyl]-N-(4-oxido-1,4λ$^4$-oxathian-4-ylidene)nicotinamide In a manner similar to that described in Example 23, 6-amino-N-(4-oxido-1,4λ$^4$-oxathian-4-ylidene)-5-[(trimethylsilyl)ethynyl]nicotinamide and N-(5-(tert-butyl)isoxazol-3-yl)-3-iodobenzamide were converted to the title compound.

$^1$H NMR (DMSO-$d_6$) δ: 11.41 (s, 1H), 8.63 (d, J=2.3 Hz, 1H), 8.31 (t, J=1.6 Hz, 1H), 8.12 (d, J=2.1 Hz, 1H), 7.99 (dt, J=7.9, 1.4 Hz, 1H), 7.91 (dt, J=7.6, 1.2 Hz, 1H), 7.58 (t, J=7.8 Hz, 1H), 7.13 (br. s., 2H), 6.73 (s, 1H), 4.12-4.17 (m, 2H), 3.94 (ddd, J=12.5, 8.7, 2.1 Hz, 2H), 3.81-3.85 (m, 2H), 3.57-3.62 (m, 2H), 1.33 (s, 9H)

Example 25

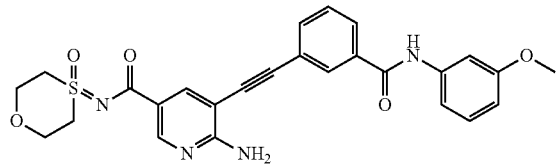 [SMILES: COc1cccc(NC(=O)c2cccc(C#Cc3cc(C(=O)N=S4(=O)CCOCC4)cnc3N)c2)c1]

6-amino-5-[(3-{[(3-methoxyphenyl)amino]carbonyl}phenyl)ethynyl]-N-(4-oxido-1,4λ⁴-oxathian-4-ylidene)nicotinamide In a manner similar to that described in Example 23, 6-amino-N-(4-oxido-1,4λ⁴-oxathian-4-ylidene)-5-[(trimethylsilyl)ethynyl]nicotinamide and 3-iodo-N-(3-methoxyphenyl)benzamide were converted to the title compound.

$^1$H NMR (DMSO-$d_6$) δ: 10.30 (s, 1H), 8.62 (d, J=2.3 Hz, 1H), 8.26 (t, J=1.5 Hz, 1H), 8.12 (d, J=2.1 Hz, 1H), 7.94 (ddd, J=7.8, 1.3, 1.2 Hz, 1H), 7.90 (dt, J=7.6, 1.2 Hz, 1H), 7.58 (t, J=7.8 Hz, 1H), 7.47 (t, J=2.2 Hz, 1H), 7.39 (dd, J=8.1, 1.0 Hz, 1H), 7.26 (t, J=8.1 Hz, 1H), 7.14 (br. s., 2H), 6.70 (dd, J=8.2, 2.1 Hz, 1H), 4.12-4.17 (m, 2H), 3.93 (ddd, J=12.5, 8.5, 1.9 Hz, 2H), 3.83 (dt, J=14.3, 2.7 Hz, 2H), 3.76 (s, 3H), 3.57-3.62 (m, 2H).

Biological data for the compounds of the present invention was generated by use of the following assays.

VEGFR2 Kinase Assay

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

VEGFR2 Cellular Assay

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by $VEGF_{165}$ stimulation (10 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

PDGFRβ Kinase Assay

Biochemical PDGFRβ kinase assays were performed in 96 well microtiter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PDGFRβ Cellular Assay

Automated FLIPR (Fluorometric Imaging Plate Reader) technology was used to screen for inhibitors of PDGF-induced increases in intracellular calcium levels in fluorescent dye loaded endothelial cells. NHDF-Ad (Normal Human Dermal Fibroblasts, Adult; Lonza) were seeded in 384-well fibronectin coated black-walled plates overnight @ 37° C./5% CO2. Cells were loaded with calcium indicator Fluo-4 for 45 minutes at 37° C. Cells were washed 2 times (E1×405, Biotek Instruments) to remove extracellular dye. For screening, cells were pre-incubated with test agents for 30 minutes, at a single concentration (10 uM) or at concentrations ranging from 0.0001 to 10.0 uM followed by PDGF-BB stimulation (30 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of PDGF-BB stimulated responses in the absence of inhibitor.

The biological results for the compounds of formula I are shown in Table 2 below.

TABLE 2

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|
| 1 | 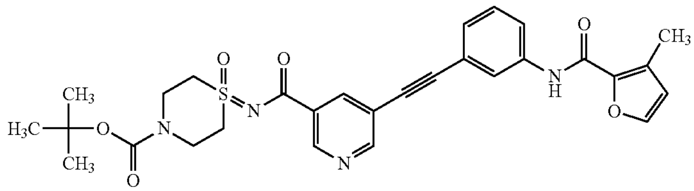 [SMILES: Cc1ccoc1C(=O)Nc1cccc(C#Cc2cncc(C(=O)N=S3(=O)CCN(C(=O)OC(C)(C)C)CC3)c2)c1] | 3 | 5 | |
| 2 | 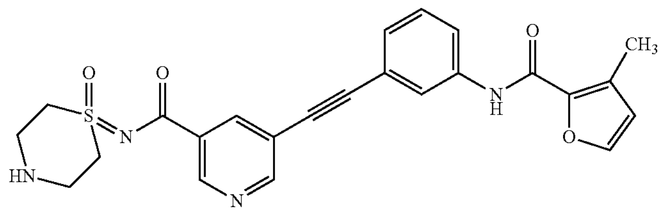 [SMILES: Cc1ccoc1C(=O)Nc1cccc(C#Cc2cncc(C(=O)N=S3(=O)CCNCC3)c2)c1] | 3 | 6 | |
| 3 | 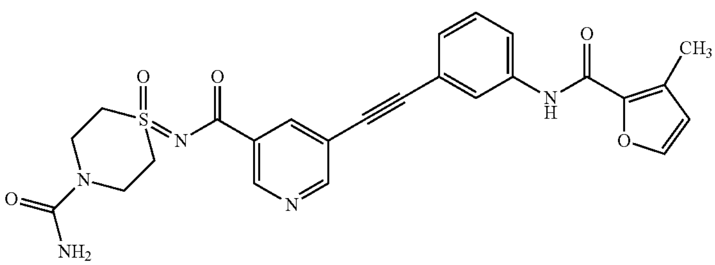 [SMILES: Cc1ccoc1C(=O)Nc1cccc(C#Cc2cncc(C(=O)N=S3(=O)CCN(C(N)=O)CC3)c2)c1] | 3 | 8 | |
| 4 | 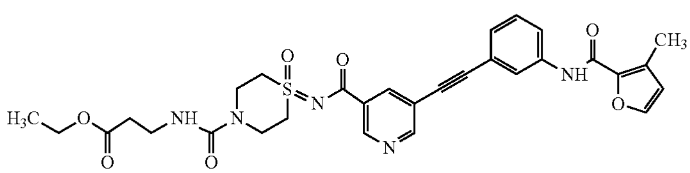 [SMILES: CCOC(=O)CCNC(=O)N1CCS(=O)(=NC(=O)c2cncc(C#Cc3cccc(NC(=O)c4occc4C)c3)c2)CC1] | 3 | 2 | |
| 5 | 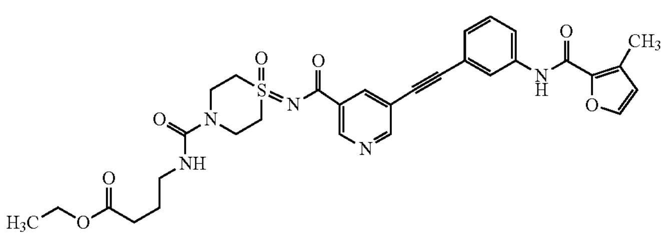 [SMILES: CCOC(=O)CCCNC(=O)N1CCS(=O)(=NC(=O)c2cncc(C#Cc3cccc(NC(=O)c4occc4C)c3)c2)CC1] | 2 | 6 | |
| 6 | 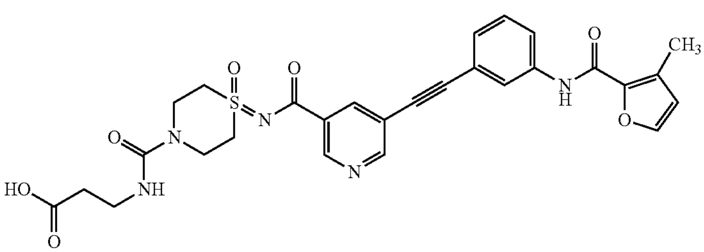 [SMILES: Cc1ccoc1C(=O)Nc1cccc(C#Cc2cncc(C(=O)N=S3(=O)CCN(C(=O)NCCC(=O)O)CC3)c2)c1] | 2 | 55 | |

TABLE 2-continued

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) |
| --- | --- | --- | --- | --- |
| 7 | 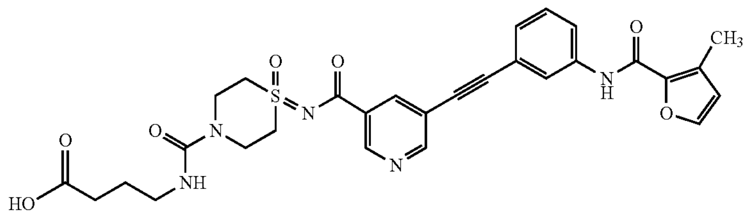 [SMILES: Cc1ccoc1C(=O)Nc1cccc(C#Cc2cncc(C(=O)N=S3(=O)CCN(C(=O)NCCCC(=O)O)CC3)c2)c1] | 2 | 22 | |
| 8 | 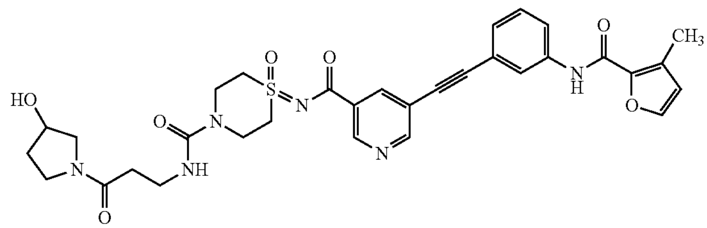 [SMILES: Cc1ccoc1C(=O)Nc1cccc(C#Cc2cncc(C(=O)N=S3(=O)CCN(C(=O)NCCC(=O)N4CCC(O)C4)CC3)c2)c1] | 4 | 36 | |
| 9 | 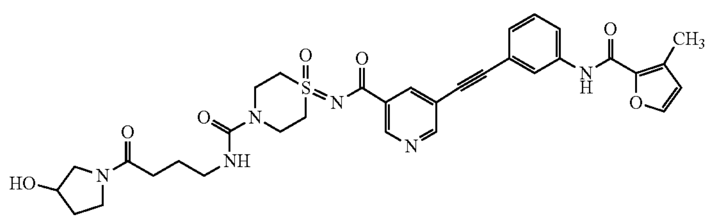 [SMILES: Cc1ccoc1C(=O)Nc1cccc(C#Cc2cncc(C(=O)N=S3(=O)CCN(C(=O)NCCCC(=O)N4CCC(O)C4)CC3)c2)c1] | 4 | 29 | |
| 10 | 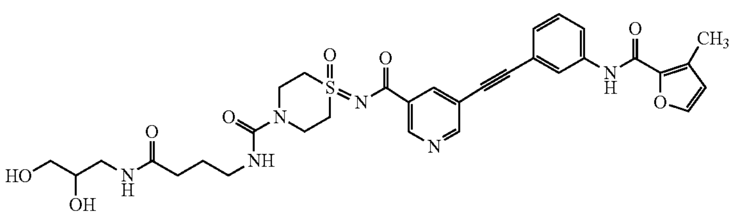 [SMILES: Cc1ccoc1C(=O)Nc1cccc(C#Cc2cncc(C(=O)N=S3(=O)CCN(C(=O)NCCCC(=O)NCC(O)CO)CC3)c2)c1] | 4 | 102 | |
| 11 | 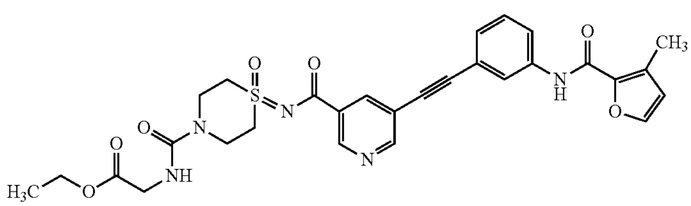 [SMILES: CCOC(=O)CNC(=O)N1CCS(=O)(=NC(=O)c2cncc(C#Cc3cccc(NC(=O)c4occc4C)c3)c2)CC1] | 5 | 7 | |
| 12 | 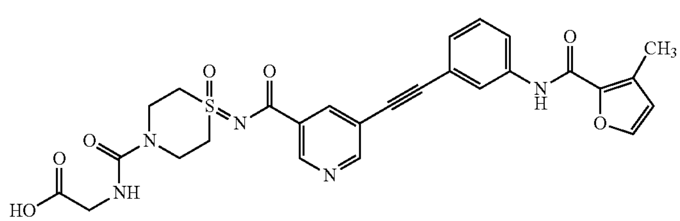 [SMILES: Cc1ccoc1C(=O)Nc1cccc(C#Cc2cncc(C(=O)N=S3(=O)CCN(C(=O)NCC(=O)O)CC3)c2)c1] | 4 | 165 | |
| 13 | 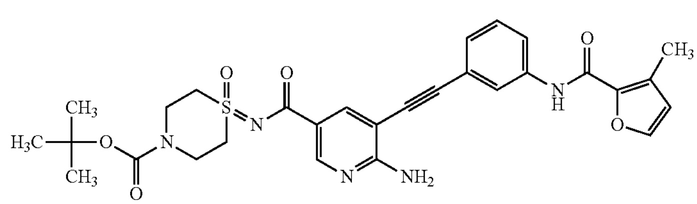 [SMILES: Cc1ccoc1C(=O)Nc1cccc(C#Cc2cc(C(=O)N=S3(=O)CCN(C(=O)OC(C)(C)C)CC3)cnc2N)c1] | 3 | 6 | |

TABLE 2-continued

| Example | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) |
|---|---|---|---|---|
| 14 | 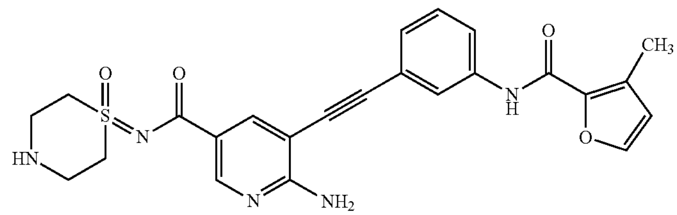 [SMILES: Cc1ccoc1C(=O)Nc1cccc(C#Cc2cc(C(=O)N=S3(=O)CCNCC3)cnc2N)c1] | 3 | 12 | |
| 15 | 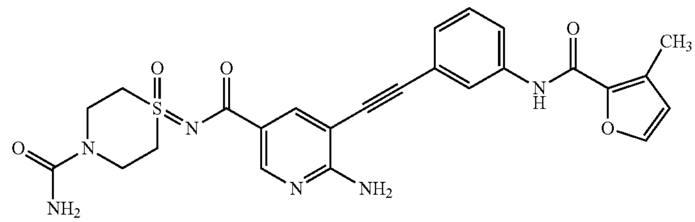 [SMILES: Cc1ccoc1C(=O)Nc1cccc(C#Cc2cc(C(=O)N=S3(=O)CCN(C(N)=O)CC3)cnc2N)c1] | 2 | 26 | |
| 16 | 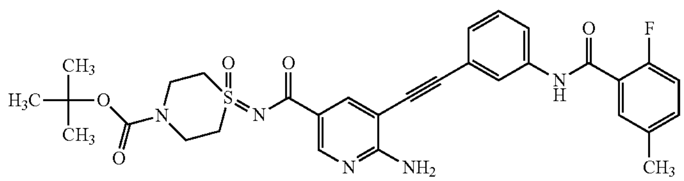 | 15 | 1 | |
| 17 | 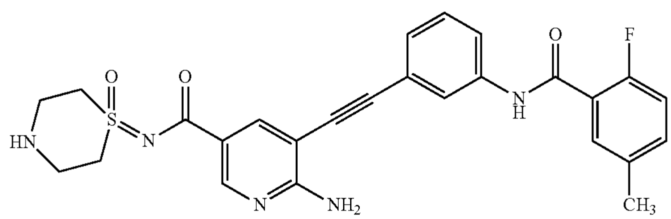 [SMILES: Cc1ccc(F)c(C(=O)Nc2cccc(C#Cc3cc(C(=O)N=S4(=O)CCNCC4)cnc3N)c2)c1] | 16 | 2 | 7 |
| 18 | 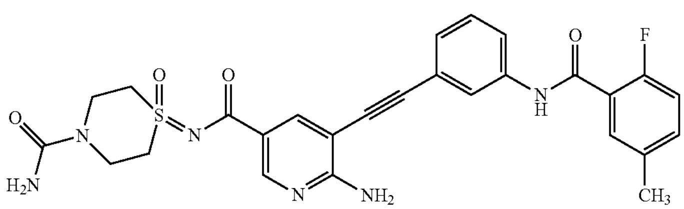 [SMILES: Cc1ccc(F)c(C(=O)Nc2cccc(C#Cc3cc(C(=O)N=S4(=O)CCN(C(N)=O)CC4)cnc3N)c2)c1] | 15 | 7 | 7 |

The biological results for compounds of formula II are shown in Table 3, below.

| Example Number | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 19 | 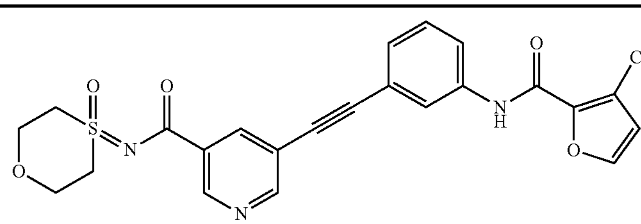 | 12 | | 23 | 19 |

-continued

| Example Number | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 20 | 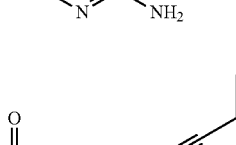 | 7 | 1 | 51 | 31 |
| 21 | 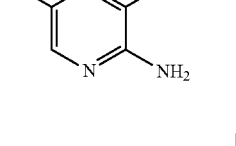 | 16 | | 24 | |
| 22 | 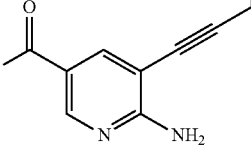 | 14 | | 11 | 17 |
| 23 | 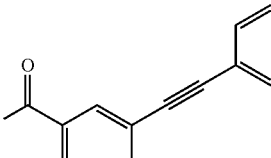 | 39 | | 13 | |
| 24 | 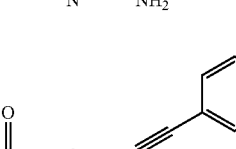 | 20 | | 10 | |
| 25 | 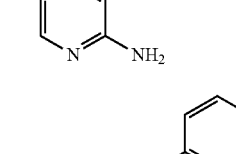 | 33 | | 19 | |

Examples 3, 11, 13, 16 and 17 are most preferred compounds of formula I, as they have the greatest potency at both VEGFR2 and PDGFRIβ receptors.

It is noted that the compounds of Examples 19 through 25 have activity at both the VEGF and PDGF receptors.

The compounds of Examples 19 and 20 have the best activity at the VEGFR2 Receptor of the compounds of formula II.

The compounds of Examples 22 and 24 have the best activity at the PDGFRβ Receptor of the compounds of formula II.

The present invention is not to be limited in scope by the exemplified embodiments which are intended as illustrations of single aspects of the invention only. Indeed, various modifications of the invention in addition to those described herein will become apparent to those skilled in the art from the foregoing description. Such modifications are intended to fall within the scope of the appended claims.

All references cited herein are hereby incorporated by reference in their entirety. Also, the compounds of the present invention may be tested by the various in-vitro and in-vivo assays disclosed in such references to demonstrate the claimed utilities.

We claim:

1. A compound of formula I or II

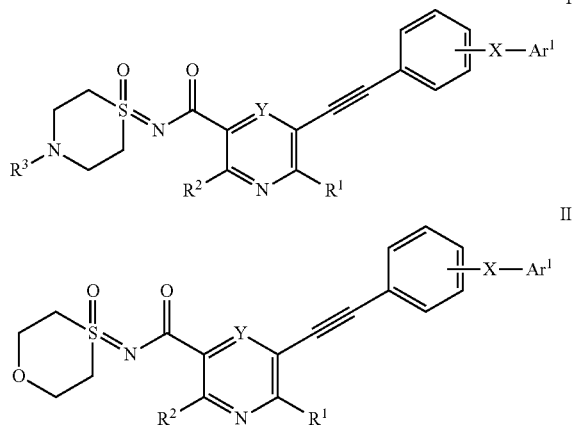

or a pharmaceutically acceptable salt thereof, wherein:
$R^1$ is hydrogen or $NH_2$;
$R^2$ is hydrogen or $NH_2$;
X is

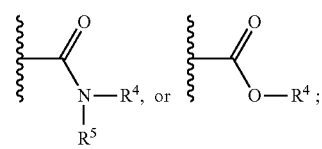

Y is CH or N;
$Ar^1$ is, in formula I, a carbocyclic aryl or heteroaryl group, wherein said carbocyclic aryl or heteroaryl group may be optionally substituted with halogen, trihalomethyl, or lower alkyl;
$Ar^1$ is, in formula II, an aryl group, i.e. a carbocyclic group or heteroaryl group, further including prodrugs, pharmaceutically acceptable salts, racemic mixtures and enantiomers thereof;
$R^3$ is hydrogen, lower alkyl,

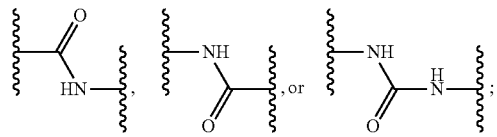

$R^4$ is hydrogen, lower alkyl, $(CH_2)_nCOOR^6$ or $(CH_2)_nCOR^7$;
$R^5$ is hydrogen or lower alkyl;
$R^6$ is hydrogen or lower alkyl;
$R^7$ is a substituted amine;
and n is 0, or an integer of from 1 to 6.

2. A compound according to claim 1 wherein X is —NH—C(O)—.

3. A compound according to claim 1 wherein Y is CH.

4. A compound according to claim 1 wherein the compound is of formula I and $Ar^1$ is selected from the group consisting of phenyl and furanyl and lower alkyl and/or halo-substituted phenyl and lower alkyl and/or halo-substituted furanyl.

5. A compound according to claim 4 wherein $Ar^1$ is selected from the group consisting of 3-methyl-2-furanyl and 2-fluoro-5-methylphenyl.

6. A compound according to claim 1 wherein, $R^2$ is H.

7. A compound according to claim 1 wherein $R^3$ is selected from the group consisting of

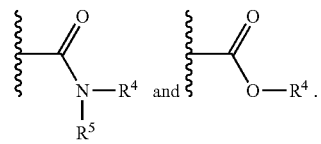

8. A compound according to claim 7 wherein $R^3$ is $C(O)N(R^4)(R^5)$.

9. The compound of claim 1 wherein $R^7$ is selected from the group consisting of

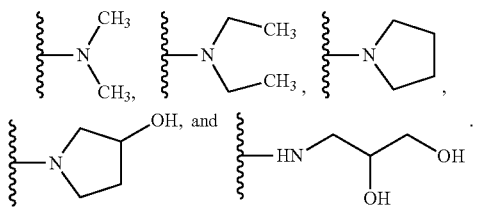

10. The compound of claim 1 wherein the compound is of formula II and said carbocyclic aryl or heteroaryl group is substituted with one or more alkoxy, halogen, trihaloalkyl, or lower alkyl groups.

11. The compound of claim 1 wherein the compound is of formula II and wherein $Ar^1$ is selected from the group consisting of phenyl, oxazoyl, furanyl and alkyl-substituted, alkyloxy-substituted and halo-substituted phenyl, oxazoyl and furanyl.

12. A compound according to claim 11 wherein $Ar^1$ is selected from the group consisting of 3-methyl-2-furanyl; 2-fluoro-5-methylphenyl 4-chloro 5-t-butylphenyl; 3-methoxyphenyl; and 5-butyloxazoyl.

13. A compound according to claim 1 wherein said compound is selected from the group consisting of:
tert-butyl 1-({[5-({3-[(3-methyl-2-furoyl)amino]phenyl}ethynyl)pyridin-3-yl]carbonyl}imino)-1λ⁴,4-thiazinane-4-carboxylate 1-oxide,
5-({3-[(3-methyl-2-furoyl)amino]phenyl}ethynyl)-N-(1-oxido-1λ⁴,4-thiazinan-1-ylidene)nicotinamide,
1-({[5-({3-[(3-methyl-2-furoyl)amino]phenyl}ethynyl)pyridin-3-yl]carbonyl}imino)-1λ⁴,4-thiazinane-4-carboxamide 1-oxide,
ethyl 3-({[1-({[5-({3-[(3-methyl-2-furoyl)amino]phenyl}ethynyl)pyridin-3-yl]carbonyl}imino)-1-oxido-1λ⁴,4-thiazinan-4-yl]carbonyl}amino)propanoate,
ethyl 4-({[1-({[5-({3-[(3-methyl-2-furoyl)amino]phenyl}ethynyl)pyridin-3-yl]carbonyl}imino)-1-oxido-1λ⁴,4-thiazinan-4-yl]carbonyl}amino)butanoate, 3-({[1-({[5-({3-[(3-methyl-2-furoyl)amino]
phenyl}ethynyl)pyridin-3-yl]carbonyl}imino)-1-
oxido-1λ⁴,4-thiazinan-4-yl]carbonyl}amino)propanoic
acid,
4-({[1-({[5-({3-[(3-methyl-2-furoyl)amino]
phenyl}ethynyl)pyridin-3-yl]carbonyl}imino)-1-
oxido-1λ⁴,4-thiazinan-4-yl]carbonyl}amino)butanoic
acid,
N-[3-(3-hydroxypyrrolidin-1-yl)-3-oxopropyl]-1-({[5-
({3-[(3-methyl-2-furoyl)amino]phenyl}ethynyl)pyri-
din-3-yl]carbonyl}imino)-1λ⁴,4-thiazinane-4-carbox-
amide 1-oxide,
N-[4-(3-hydroxypyrrolidin-1-yl)-4-oxobutyl]-1-({[5-({3-
[(3-methyl-2-furoyl)amino]phenyl}ethynyl)pyridin-3-
yl]carbonyl}imino)-1λ⁴,4-thiazinane-4-carboxamide
1-oxide;
N-{4-[(2,3-dihydroxypropyl)amino]-4-oxobutyl}-1-({[5-
({3-[(3-methyl-2-furoyl)amino]phenyl}ethynyl)pyri-
din-3-yl]carbonyl}imino)-1λ⁴,4-thiazinane-4-carbox-
amide 1-oxide,
ethyl({[1-({[5-({3-[(3-methyl-2-furoyl)amino]
phenyl}ethynyl)pyridin-3-yl]carbonyl}imino)-1-
oxido-1λ⁴,4-thiazinan-4-yl]carbonyl}amino)acetate,
({[1-({[5-({3-[(3-methyl-2-furoyl)amino]
phenyl}ethynyl)pyridin-3-yl]carbonyl}imino)-1-
oxido-1λ⁴,4-thiazinan-4-yl]carbonyl}amino)acetic
acid,
tert-butyl 1-({[6-amino-5-({3-[(3-methyl-2-furoyl)
amino]phenyl}ethynyl)pyridin-3-yl]carbonyl}imino)-
1λ⁴,4-thiazinane-4-carboxylate 1-oxide,
6-amino-5-({3-[(3-methyl-2-furoyl)amino]
phenyl}ethynyl)-N-(1-oxido-1λ⁴,4-thiazinan-1-
ylidene)nicotinamide,
1-({[6-amino-5-({3-[(3-methyl-2-furoyl)amino]
phenyl}ethynyl)pyridin-3-yl]carbonyl}imino)-1λ⁴,4-
thiazinane-4-carboxamide 1-oxide,
tert-butyl 1-({[6-amino-5-({3-[(2-fluoro-5-methylben-
zoyl)amino]phenyl}ethynyl)pyridin-3-yl]
carbonyl}imino)-1λ⁴,4-thiazinane-4-carboxylate 1-ox-
ide,
6-amino-5-({3-[(2-fluoro-5-methylbenzoyl)amino]
phenyl}ethynyl)-N-(1-oxido-1λ⁴,4-thiazinan-1-
ylidene)nicotinamide,
1-({[6-amino-5-({3-[(2-fluoro-5-methylbenzoyl)amino]
phenyl}ethynyl)pyridin-3-yl]carbonyl}imino)-1λ⁴,4-
thiazinane-4-carboxamide 1-oxide;
5-({3-[(3-methyl-2-furoyl)amino]phenyl}ethynyl)-N-(4-
oxido-1,4λ⁴-oxathian-4-ylidene)nicotinamide,
6-amino-5-({3-[(3-methyl-2-furoyl)amino]
phenyl}ethynyl)-N-(4-oxido-1,4λ⁴-oxathian-4-
ylidene)nicotinamide,
6-amino-5-({3-[(2-fluoro-5-methylbenzoyl)amino]
phenyl}ethynyl)-N-(4-oxido-1,4λ⁴-oxathian-4-
ylidene)nicotinamide,
6-amino-5-[(3-{[(2-fluoro-5-methylphenyl)amino]
carbonyl}phenyl)ethynyl]-N-(4-oxido-1,4λ⁴-oxathian-
4-ylidene)nicotinamide,
6-amino-5-{[3-({[4-chloro-3-(trifluoromethyl)phenyl]
amino}carbonyl)phenyl]ethynyl}-N-(4-oxido-1,4λ⁴-
oxathian-4-ylidene)nicotinamide,
6-amino-5-[(3-{[(5-tert-butylisoxazol-3-yl)amino]
carbonyl}phenyl)ethynyl]-N-(4-oxido-1,4λ⁴-oxathian-
4-ylidene)nicotinamide, and
6-amino-5-[(3-{[(3-methoxyphenyl)amino]
carbonyl}phenyl)ethynyl]-N-(4-oxido-1,4λ⁴-oxathian-
4-ylidene)nicotinamide;
or a pharmaceutically acceptable salt thereof or a pharmaceutically acceptable salt thereof.

14. The compound of claim 1 that is 5-({3-[(3-methyl-2-furoyl)amino]phenyl}ethynyl)-N-(4-oxido-1,4λ⁴-oxathian-4-ylidene)nicotinamide, or a pharmaceutically acceptable salt thereof.

15. The compound of claim 1 that is 6-amino-5-({3-[(3-methyl-2-furoyl)amino]phenyl}ethynyl)-N-(4-oxido-1,4λ⁴-oxathian-4-ylidene)nicotinamide, or a pharmaceutically acceptable salt thereof.

16. The compound of claim 1 that is 6-amino-5-[(3-{[(2-fluoro-5-methylphenyl)amino]carbonyl}phenyl)ethynyl]-N-(4-oxido-1,4λ⁴-oxathian-4-ylidene)nicotinamide, or a pharmaceutically acceptable salt thereof.

17. The compound of claim 1 that is 6-amino-5-[(3-{[(5-tert-butylisoxazol-3-yl)amino]carbonyl}phenyl)ethynyl]-N-(4-oxido-1,4λ⁴-oxathian-4-ylidene)nicotinamide, or a pharmaceutically acceptable salt thereof.

\* \* \* \* \*

UNITED STATES PATENT AND TRADEMARK OFFICE
CERTIFICATE OF CORRECTION

| | |
|---|---|
| PATENT NO. | : 9,567,324 B2 |
| APPLICATION NO. | : 15/069344 |
| DATED | : February 14, 2017 |
| INVENTOR(S) | : Boral et al. |

It is certified that error appears in the above-identified patent and that said Letters Patent is hereby corrected as shown below:

On the Title Page

Column 2, item [56], under "Other Publications", Line 24, delete "Chemica" and insert -- Chimica --, therefor.

In the Specification

Column 2, Line 30, delete "Opthalmologica" and insert -- Ophthalmologica --, therefor.

Column 3, Line 45, after "N" insert -- , --.

Column 4, Line 13, delete "e.g.lower" and insert -- e.g. lower --, therefor.

Column 5, Line 2, after "NH—" insert -- . --.

Column 5, Line 5, delete "oxazoyl" and insert -- oxazolyl --, therefor.

Column 5, Line 6, delete "oxazoyl" and insert -- oxazolyl --, therefor.

Column 5, Line 10, delete "fluoro 5" and insert -- fluoro-5 --, therefor.

Column 5, Line 10, delete "chloro 5" and insert -- chloro-5 --, therefor.

Column 5, Line 12, delete "-butyloxazoyl." and insert -- -butyloxazolyl. --, therefor.

Column 6, Line 34, delete "pterigium," and insert -- pterygium, --, therefor.

Column 6, Line 36, delete "diabetis" and insert -- diabetes --, therefor.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*

Column 7, Line 18, delete "degeneratuon)" and insert -- degeneration) --, therefor.

Column 7, Line 28, delete "phosphoniumhexafluorophnosphate" and insert -- phosphoniumhexafluorophosphate --, therefor.

Column 8, Line 17, delete "tartarates," and insert -- tartrates, --, therefor.

Column 8, Line 25, delete "J" and insert -- J. --, therefor.

Column 23, Line 32, after "9H)" insert -- . --.

Column 23, Line 54, delete "dixane" and insert -- dioxane --, therefor.

Column 24, Line 12, after "9H)" insert -- . --.

Column 24, Line 54, after "9H)" insert -- . --.

Column 25, Line 2, delete "carbony}" and insert -- carbonyl} --, therefor.

Column 25, Line 22, after "9H)" insert -- . --.

Column 26, Line 33, after "3H)" insert -- . --.

Column 26, Line 67, after "3H)" insert -- . --.

Column 27, Line 21, delete "-({3[" and insert -- -({3-[ --, therefor.

Column 27, Line 28, delete "nicotinamide_" and insert -- nicotinamide --, therefor.

Column 28, Line 32, after "3H)" insert -- . --.

Column 28, Line 67, after "3H)" insert -- . --.

Column 29, Line 28, delete "treatd" and insert -- treated --, therefor.

Column 30, Line 20, delete "resiude" and insert -- residue --, therefor.

Column 30, Line 57, delete "carbonyl}" and insert -- carbonyl}amino) --, therefor.

Column 30, Line 67, after "2H)" insert -- . --.

Column 31, Line 24, delete "carbonyl}" and insert -- carbonyl}amino) --, therefor.

Column 32, Lines 60-67, delete "J=2.1 Hz, 1H), 8.13 (t, J=1.6 Hz, 1H), 7.76-7.83 (m,

CERTIFICATE OF CORRECTION (continued)
U.S. Pat. No. 9,567,324 B2

3H), 7.39-7.43 (m, 1H), 7.34 (d, J=7.8 Hz, 1H), 6.90 (t, J=5.1 Hz, 1H), 6.61 (d, J=1.5 Hz, 1H), 4.72 (d, J=4.9 Hz, 1H), 4.50 (t, J=5.9 Hz, 1H), 4.06-4.12 (m, 2H), 3.77-3.83 (m, 2H), 3.61 (dd, J=13.4, 9.8 Hz, 2H), 3.44-3.52 (m, 3H), 3.26 (dtd, J=10.5, 5.5, 5.3 Hz, 2H), 3.18 (ddd, J=13.3, 5.6, 5.5 Hz, 1H), 3.01-3.07 (m, 2H), 2.93-2.99 (m, 1H), 2.35 (s, 3H), 2.11 (t, J=7.5 Hz, 2H), 1.65 (dt, J=14.5, 7.3 Hz, 2H)" and insert the same on Column 32, Line 59, as a continuation of the same paragraph.

Column 32, Line 67, after "2H)" insert -- . --.

Column 33, Line 17, delete "Ethyl({" and insert -- Ethyl ({ --, therefor.

Column 33, Line 29, after "3H)" insert -- . --.

Column 34, Line 52, after "3H)" insert -- . --.

Column 35, Line 20, delete "9H" and insert -- 9H). --, therefor.

Column 35, Line 67, after "3H)" insert -- . --.

Column 36, Line 32, after "3H)" insert -- . --.

Column 36, Line 67, after "9H)" insert -- . --.

Column 37, Line 31, after "3H)" insert -- . --.

Column 37, Line 67, after "3H)" insert -- . --.

Column 38, Line 27, after "3H)" insert -- . --.

Column 38, Line 50, after "2H)" insert -- . --.

Column 39, Line 14, after "2H)" insert -- . --.

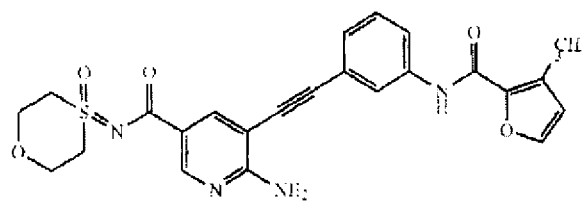

Column 39, Lines 16-26, delete " " and insert

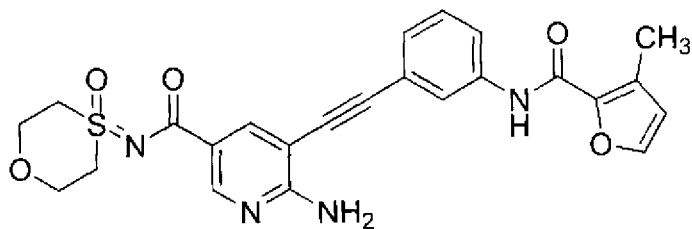

-- --, therefor.

Column 39, Line 43, delete "NH4Cl" and insert -- NH4Cl, --, therefor.

Column 39, Line 54, after "3H)" insert -- . --.

Column 40, Line 14, after "3H)" insert -- . --.

Column 40, Lines 20-28, delete " 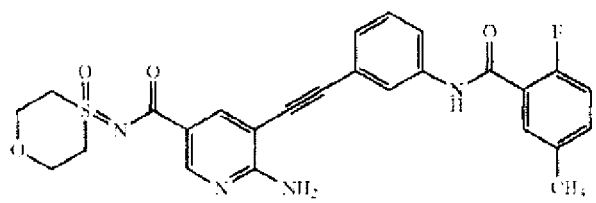 " and insert

-- --, therefor.

Column 40, Line 44, after "3H)" insert -- . --.

Column 40, Line 65, delete "NH4Cl" and insert -- NH4Cl, --, therefor.

Column 41, Line 9, after "1H)" insert -- . --.

Column 42, Line 10, delete "–CHCl₃1:50)." and insert -- –CHCl₃ 1:50)." --, therefor.

Column 42, Line 20, after "2H)" insert -- . --.

Column 42, Line 53, after "9H)" insert -- . --.

Column 44, Line 55, delete "(E1×405," and insert -- (El×405, --, therefor.

Column 51, Line 62, delete "PDGFRIβ" and insert -- PDGFRβ --, therefor.

CERTIFICATE OF CORRECTION (continued)
U.S. Pat. No. 9,567,324 B2

In the Claims

Column 54, Line 24, Claim 8, delete "C(O)" and insert -- –C(O) --, therefor.

Column 54, Line 44, Claim 11, delete "oxazoyl," and insert -- oxazolyl, --, therefor.

Column 54, Line 45, Claim 11, delete "oxazoyl" and insert -- oxazolyl --, therefor.

Column 54, Line 48, Claim 12, after "methylphenyl" insert -- ; --.

Column 54, Line 48, Claim 12, delete "chloro 5" and insert -- chloro-5 --, therefor.

Column 54, Line 49, Claim 12, delete "-butyloxazoyl." and insert -- -butyloxazolyl. --, therefor.

Column 55, Line 16, Claim 13, delete "-oxide;" and insert -- -oxide, --, therefor.

Column 55, Line 21, Claim 13, delete "ethyl(" and insert -- ethyl ( --, therefor.

Column 56, Line 3, Claim 13, delete "-oxide;" and insert -- -oxide, --, therefor.

Column 56, Lines 24-25, Claim 13, delete "thereof or a pharmaceutically acceptable salt thereof." and insert -- thereof. --, therefor.